(12) United States Patent
Moeller et al.

(10) Patent No.: US 12,214,017 B2
(45) Date of Patent: *Feb. 4, 2025

(54) GLP-1 COMPOSITIONS AND USES THEREOF

(71) Applicant: Novo Nordisk A/S, Bagsvaerd (DK)

(72) Inventors: Eva Horn Moeller, Alleroed (DK); Michael Duelund Soerensen, Soeborg (DK); Joakim Lundqvist, Malmoe (SE)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/427,270

(22) Filed: Jan. 30, 2024

(65) Prior Publication Data

US 2024/0216475 A1   Jul. 4, 2024

Related U.S. Application Data

(63) Continuation of application No. 18/226,405, filed on Jul. 26, 2023, which is a continuation of application No. 17/115,773, filed on Dec. 8, 2020, now Pat. No. 11,752,198, which is a continuation of application No. 16/774,666, filed on Jan. 28, 2020, now Pat. No. 10,888,605, which is a continuation of application No. PCT/EP2018/072835, filed on Aug. 24, 2018.

(30) Foreign Application Priority Data

Aug. 24, 2017   (EP) ..................... 17187676

(51) Int. Cl.
| | | |
|---|---|---|
| A61K 38/26 | (2006.01) | |
| A61K 9/00 | (2006.01) | |
| A61K 9/08 | (2006.01) | |
| A61K 47/02 | (2006.01) | |
| A61K 47/10 | (2017.01) | |

(52) U.S. Cl.
CPC ............ *A61K 38/26* (2013.01); *A61K 9/0019* (2013.01); *A61K 9/08* (2013.01); *A61K 47/02* (2013.01); *A61K 47/10* (2013.01)

(58) Field of Classification Search
CPC ........ A61K 38/26; A61K 9/0019; A61K 9/08; A61K 47/02; A61K 47/10
See application file for complete search history.

(56) References Cited

U.S. PATENT DOCUMENTS

| | | |
|---|---|---|
| 2,444,570 A | 8/1946 | Lawrence et al. |
| 2,828,742 A | 4/1958 | Ashkenaz |
| 3,318,289 A | 5/1967 | Marynissen |
| 3,758,683 A | 9/1973 | Jackson |
| 4,282,316 A | 8/1981 | Modrovich |
| 4,425,346 A | 1/1984 | Horlington |
| 4,468,346 A | 8/1984 | Paul et al. |
| 4,470,317 A | 9/1984 | Sabloewski et al. |
| 4,483,849 A | 11/1984 | Carter et al. |
| 4,498,904 A | 2/1985 | Turner et al. |
| 4,568,335 A | 2/1986 | Updike et al. |
| 4,585,439 A | 4/1986 | Michel |
| 4,592,745 A | 6/1986 | Rex et al. |
| 4,629,455 A | 12/1986 | Kanno |
| 4,833,379 A | 5/1989 | Kaibel et al. |
| 4,865,591 A | 9/1989 | Sams |
| 4,883,472 A | 11/1989 | Michel |
| 4,917,685 A | 4/1990 | Viswanathan et al. |
| 4,919,596 A | 4/1990 | Slate et al. |
| 4,936,833 A | 6/1990 | Sams |
| 4,973,318 A | 11/1990 | Holm et al. |
| 4,994,033 A | 2/1991 | Shockey et al. |
| 5,017,190 A | 5/1991 | Simon et al. |
| 5,092,842 A | 3/1992 | Bechtold et al. |
| 5,112,317 A | 5/1992 | Michel |
| 5,114,406 A | 5/1992 | Gabriel et al. |
| 5,118,666 A | 6/1992 | Habener |
| 5,120,712 A | 6/1992 | Habener |
| 5,169,771 A | 12/1992 | Christner et al. |
| 5,206,216 A | 4/1993 | Yoshida |
| 5,206,219 A | 4/1993 | Desai |
| 5,207,752 A | 5/1993 | Sorenson et al. |
| 5,216,011 A | 6/1993 | Paborji et al. |
| 5,216,437 A | 6/1993 | Yamamoto et al. |
| 5,226,895 A | 7/1993 | Harris |
| 5,232,459 A | 8/1993 | Hjertman |
| 5,232,706 A | 8/1993 | Palomo Coll |

(Continued)

FOREIGN PATENT DOCUMENTS

| | | |
|---|---|---|
| AU | 611385 B2 | 6/1991 |
| CA | 2223531 A1 | 12/1996 |

(Continued)

OTHER PUBLICATIONS

Basf: "Basf Chemical Emergency Medical Guidelines," Jan. 1, 2016, Retrieved from the Internet: URL: https://www.basf.com/documents/corp/en/sustainability/employees-and-society/employees/occupational-medicine/medical-guidelines/Phenol_B_BASF_medGuidelines_E104. pdf, retrieved on Nov. 20, 2017.
Lau et al., Journal of Medicinal Chemistry, 2015, vol. 58, No. 18, pp. 7370-7380.
Marbury et al., "Pharmacokinetics and Tolerability of a Single Dose of Semaglutide, a Once-Weekly Human GLP-1 Analogue, in Subjects With and Without Renal Impairment," Diabetologia, 2014, vol. 57, Supplement: 1, pp. S358-S359.
Gennaro, Remington Pharmacy 2003, 20th Edition, No. 1 Chapter 38, pp. 815-837.

(Continued)

*Primary Examiner* — Sudhakar Katakam
(74) *Attorney, Agent, or Firm* — Elizabeth A. Dingess-Hammond; Rosemarie A. Wilk-Orescan

(57) ABSTRACT

The present invention relates to pharmaceutical compositions of the GLP-1 peptide semaglutide comprising no more than 0.01% (w/w) phenol, their preparation, kits comprising such compositions as well as uses thereof.

9 Claims, No Drawings

(56) References Cited

U.S. PATENT DOCUMENTS

| | | |
|---|---|---|
| 5,246,417 A | 9/1993 | Haak et al. |
| 5,257,987 A | 11/1993 | Athayde et al. |
| 5,271,527 A | 12/1993 | Haber et al. |
| 5,272,135 A | 12/1993 | Takruri |
| 5,279,585 A | 1/1994 | Balkwill |
| 5,279,586 A | 1/1994 | Balkwill |
| 5,281,198 A | 1/1994 | Haber et al. |
| 5,284,480 A | 2/1994 | Porter et al. |
| 5,304,152 A | 4/1994 | Sams |
| 5,308,340 A | 5/1994 | Harris |
| 5,314,412 A | 5/1994 | Rex |
| 5,318,540 A | 6/1994 | Athayde et al. |
| 5,320,609 A | 6/1994 | Haber et al. |
| 5,331,954 A | 7/1994 | Rex et al. |
| 5,370,629 A | 12/1994 | Michel et al. |
| 5,378,233 A | 1/1995 | Haber et al. |
| 5,380,297 A | 1/1995 | Wadman et al. |
| 5,383,166 A | 1/1995 | Gallay |
| 5,383,865 A | 1/1995 | Michel |
| 5,440,976 A | 8/1995 | Giuliano et al. |
| 5,445,606 A | 8/1995 | Haak et al. |
| 5,447,150 A | 9/1995 | Bacon |
| 5,455,331 A | 10/1995 | Pearce |
| 5,461,031 A | 10/1995 | De Felippis |
| 5,478,316 A | 12/1995 | Bitdinger et al. |
| 5,478,324 A | 12/1995 | Meyer |
| 5,480,387 A | 1/1996 | Gabriel et al. |
| 5,492,534 A | 2/1996 | Athayde et al. |
| 5,505,704 A | 4/1996 | Pawelka et al. |
| 5,512,549 A | 4/1996 | Chen et al. |
| 5,514,097 A | 5/1996 | Knauer |
| 5,545,147 A | 8/1996 | Harris |
| 5,545,618 A | 8/1996 | Buckley et al. |
| 5,546,932 A | 8/1996 | Galli |
| 5,549,574 A | 8/1996 | Townsend |
| 5,549,575 A | 8/1996 | Giambattista et al. |
| 5,571,719 A | 11/1996 | Christensen et al. |
| 5,574,008 A | 11/1996 | Johnson et al. |
| 5,584,815 A | 12/1996 | Pawelka et al. |
| 5,591,136 A | 1/1997 | Gabriel |
| 5,599,314 A | 2/1997 | Neill |
| 5,611,783 A | 3/1997 | Mikkelsen |
| 5,614,492 A | 3/1997 | Habener |
| 5,626,566 A | 5/1997 | Petersen et al. |
| 5,645,052 A | 7/1997 | Kersey |
| 5,652,216 A | 7/1997 | Kornfelt et al. |
| 5,674,204 A | 10/1997 | Chanoch |
| 5,679,111 A | 10/1997 | Hjertman et al. |
| 5,681,285 A | 10/1997 | Ford et al. |
| 5,685,864 A | 11/1997 | Shanley et al. |
| 5,686,411 A | 11/1997 | Gaeta et al. |
| 5,688,251 A | 11/1997 | Chanoch |
| 5,693,027 A | 12/1997 | Hansen et al. |
| 5,693,520 A | 12/1997 | Branner et al. |
| 5,693,608 A | 12/1997 | Bechgaard et al. |
| 5,705,483 A | 1/1998 | Galloway et al. |
| 5,709,662 A | 1/1998 | Olive et al. |
| 5,716,990 A | 2/1998 | Bagshawe et al. |
| 5,725,508 A | 3/1998 | Chanoch et al. |
| 5,741,688 A | 4/1998 | Oxenbøll et al. |
| 5,743,889 A | 4/1998 | Sams |
| 5,750,140 A | 5/1998 | Weibel et al. |
| 5,755,692 A | 5/1998 | Manicom |
| 5,823,998 A | 10/1998 | Yamagata |
| 5,827,232 A | 10/1998 | Chanoch et al. |
| 5,843,036 A | 12/1998 | Olive et al. |
| 5,849,700 A | 12/1998 | Sørensen et al. |
| 5,882,718 A | 3/1999 | Pommer et al. |
| 5,898,028 A | 4/1999 | Jensen et al. |
| 5,908,830 A | 6/1999 | Smith et al. |
| 5,921,966 A | 7/1999 | Bendek et al. |
| 5,928,201 A | 7/1999 | Poulsen et al. |
| 5,932,547 A | 8/1999 | Stevenson et al. |
| 5,938,642 A | 8/1999 | Burroughs et al. |
| 5,947,934 A | 9/1999 | Hansen et al. |
| 5,951,530 A | 9/1999 | Steengaard et al. |
| 5,954,689 A | 9/1999 | Poulsen |
| 5,961,496 A | 10/1999 | Nielsen et al. |
| 5,962,407 A | 10/1999 | Kelly |
| 5,972,873 A | 10/1999 | Nielsen et al. |
| 5,980,491 A | 11/1999 | Hansen |
| 5,981,489 A | 11/1999 | Stevenson et al. |
| 5,984,900 A | 11/1999 | Mikkelsen |
| 5,985,629 A | 11/1999 | Aaslyng et al. |
| 5,989,169 A | 11/1999 | Svendsen et al. |
| 6,003,736 A | 12/1999 | Ljunggren |
| 6,004,297 A | 12/1999 | Steenfeldt-Jensen et al. |
| 6,010,485 A | 1/2000 | Buch-Rasmussen et al. |
| 6,033,376 A | 3/2000 | Rockley |
| 6,033,377 A | 3/2000 | Rasmussen et al. |
| 6,048,336 A | 4/2000 | Gabriel |
| 6,059,616 A | 5/2000 | Bluemmel et al. |
| 6,066,619 A | 5/2000 | Stevenson et al. |
| 6,074,372 A | 6/2000 | Hansen |
| 6,083,197 A | 7/2000 | Umbaugh |
| 6,086,567 A | 7/2000 | Kirchhofer et al. |
| 6,096,010 A | 8/2000 | Walters et al. |
| 6,110,149 A | 8/2000 | Klitgaard et al. |
| 6,129,080 A | 10/2000 | Pitcher et al. |
| 6,133,229 A | 10/2000 | Gibson et al. |
| 6,136,784 A | 10/2000 | L'Italien et al. |
| 6,146,361 A | 11/2000 | DiBiasi et al. |
| 6,184,201 B1 | 2/2001 | Drucker et al. |
| 6,193,698 B1 | 2/2001 | Kirchhofer et al. |
| 6,207,684 B1 | 3/2001 | Aberg |
| 6,221,046 B1 | 4/2001 | Burroughs et al. |
| 6,221,053 B1 | 4/2001 | Walters et al. |
| 6,231,540 B1 | 5/2001 | Smedegaard |
| 6,235,004 B1 | 5/2001 | Steenfeldt-Jensen et al. |
| 6,245,572 B1 | 6/2001 | Wall |
| 6,248,090 B1 | 6/2001 | Jensen et al. |
| 6,248,095 B1 | 6/2001 | Giambattista et al. |
| 6,258,062 B1 | 7/2001 | Thielen et al. |
| 6,268,343 B1 | 7/2001 | Knudsen et al. |
| 6,269,340 B1 | 7/2001 | Ford et al. |
| 6,274,553 B1 | 8/2001 | Furuya et al. |
| 6,277,097 B1 | 8/2001 | Mikkelsen et al. |
| 6,277,098 B1 | 8/2001 | Klitmose et al. |
| 6,281,225 B1 | 8/2001 | Hearst et al. |
| 6,283,941 B1 | 9/2001 | Schoenfeld et al. |
| 6,284,727 B1 | 9/2001 | Kim et al. |
| 6,287,283 B1 | 9/2001 | Ljunggreen et al. |
| 6,302,869 B1 | 10/2001 | Klitgaard |
| 6,303,661 B1 | 10/2001 | Demuth et al. |
| 6,312,413 B1 | 11/2001 | Jensen et al. |
| 6,340,357 B1 | 1/2002 | Poulsen et al. |
| 6,375,975 B1 | 4/2002 | Modi |
| 6,379,339 B1 | 4/2002 | Klitgaard et al. |
| 6,380,357 B2 | 4/2002 | Hermeling et al. |
| 6,384,016 B1 | 5/2002 | Kaarsholm |
| 6,440,460 B1 | 8/2002 | Gurny et al. |
| 6,440,930 B1 | 8/2002 | Rinella, Jr. |
| 6,444,788 B1 | 9/2002 | Staby |
| 6,458,924 B2 | 10/2002 | Knudsen et al. |
| 6,489,292 B1 | 12/2002 | Havelund et al. |
| 6,514,230 B1 | 2/2003 | Munk et al. |
| 6,547,763 B2 | 4/2003 | Steenfeldt-Jensen et al. |
| 6,547,764 B2 | 4/2003 | Larsen et al. |
| 6,551,992 B1 | 4/2003 | DeFelippis et al. |
| 6,562,006 B1 | 5/2003 | Hjertman et al. |
| 6,562,011 B1 | 5/2003 | Buch-Rasmussen et al. |
| 6,569,126 B1 | 5/2003 | Poulsen et al. |
| 6,569,832 B1 | 5/2003 | Knudsen et al. |
| 6,573,237 B2 | 6/2003 | Rinella, Jr. |
| 6,582,404 B1 | 6/2003 | Klitgaard et al. |
| 6,586,399 B1 | 7/2003 | Drucker |
| 6,605,067 B1 | 8/2003 | Larsen |
| 6,613,019 B2 | 9/2003 | Munk |
| 6,660,716 B1 | 12/2003 | Yakubu-Madus et al. |
| 6,663,602 B2 | 12/2003 | Moller |
| 6,692,472 B2 | 2/2004 | Hansen et al. |
| 6,708,846 B1 | 3/2004 | Fuchs et al. |
| 6,716,198 B2 | 4/2004 | Larsen |
| 6,726,661 B2 | 4/2004 | Munk et al. |

(56) References Cited

U.S. PATENT DOCUMENTS

| | | |
|---|---|---|
| 6,770,288 B2 | 8/2004 | Duirs |
| 6,796,970 B1 | 9/2004 | Klitmose et al. |
| 6,844,321 B2 | 1/2005 | Arentsen |
| 6,893,415 B2 | 5/2005 | Madsen et al. |
| 6,899,698 B2 | 5/2005 | Sams |
| 6,899,699 B2 | 5/2005 | Enggaard |
| 6,945,961 B2 | 9/2005 | Miller et al. |
| 7,008,399 B2 | 3/2006 | Larsen et al. |
| 7,022,674 B2 | 4/2006 | DeFelippis et al. |
| 7,049,284 B2 | 5/2006 | Drucker |
| 7,056,886 B2 | 6/2006 | Isaacs |
| 7,090,662 B2 | 8/2006 | Wimpenny et al. |
| 7,094,221 B2 | 8/2006 | Veasey et al. |
| 7,104,972 B2 | 9/2006 | Moller et al. |
| 7,112,187 B2 | 9/2006 | Karlsson |
| 7,112,567 B2 | 9/2006 | Bridon et al. |
| 7,133,329 B2 | 11/2006 | Skyggebjerg et al. |
| 7,175,055 B2 | 2/2007 | Hansen et al. |
| 7,202,213 B2 | 4/2007 | Mogensen et al. |
| 7,226,990 B2 | 6/2007 | Knudsen et al. |
| 7,235,627 B2 | 6/2007 | Knudson et al. |
| 7,238,663 B2 | 7/2007 | DeFelippis et al. |
| 7,241,278 B2 | 7/2007 | Moller |
| 7,273,921 B2 | 9/2007 | Dunweber et al. |
| 7,595,293 B2 | 9/2009 | Engelund et al. |
| 7,632,806 B2 | 12/2009 | Juul-Mortensen et al. |
| 7,833,531 B2 | 11/2010 | O'Neil et al. |
| 8,071,103 B2 | 12/2011 | O'Neil et al. |
| 8,114,833 B2 | 2/2012 | Pedersen et al. |
| 8,129,343 B2 | 3/2012 | Lau et al. |
| 8,158,583 B2 | 4/2012 | Knudsen et al. |
| RE43,834 E | 11/2012 | Steenfeldt-Jensen et al. |
| 8,541,470 B2 | 9/2013 | Davis |
| 8,759,291 B2 | 6/2014 | Young et al. |
| 8,846,618 B2 | 9/2014 | Flink et al. |
| 9,133,276 B2 | 9/2015 | Cleemann et al. |
| 9,217,022 B2 | 12/2015 | Alfaro-Lopez et al. |
| 9,265,723 B2 | 2/2016 | Sprogoe et al. |
| 9,457,066 B2 | 10/2016 | Rau et al. |
| 9,764,003 B2 | 9/2017 | Jensen |
| 10,888,605 B2 | 1/2021 | Moeller et al. |
| 11,572,398 B2 | 2/2023 | Sauerberg et al. |
| 11,752,198 B2 * | 9/2023 | Moeller .......... A61P 3/04 530/300 |
| 2001/0014666 A1 | 8/2001 | Hermeling et al. |
| 2001/0027180 A1 | 10/2001 | Isaacs |
| 2002/0007154 A1 | 1/2002 | Hansen et al. |
| 2002/0052578 A1 | 5/2002 | Moller |
| 2002/0061838 A1 | 5/2002 | Holmquist et al. |
| 2002/0077852 A1 | 6/2002 | Ford et al. |
| 2002/0120235 A1 | 8/2002 | Enggaard |
| 2002/0151467 A1 | 10/2002 | Leung |
| 2003/0039679 A1 | 2/2003 | Duirs |
| 2003/0045838 A1 | 3/2003 | Woodard et al. |
| 2003/0060412 A1 | 3/2003 | Prouty et al. |
| 2003/0069182 A1 | 4/2003 | Rinella |
| 2003/0092606 A1 | 5/2003 | L'Italien et al. |
| 2003/0092612 A1 | 5/2003 | Lyons |
| 2003/0119734 A1 | 6/2003 | Flink et al. |
| 2003/0158101 A1 | 8/2003 | Drucker |
| 2003/0172924 A1 | 9/2003 | Staniforth et al. |
| 2003/0207802 A1 | 11/2003 | DeFelippis et al. |
| 2003/0211047 A1 | 11/2003 | Dugger |
| 2003/0220243 A1 | 11/2003 | Glaesner et al. |
| 2003/0220255 A1 | 11/2003 | Knudsen et al. |
| 2004/0059299 A1 | 3/2004 | Moller |
| 2004/0156835 A1 | 8/2004 | Imoto et al. |
| 2004/0186431 A1 | 9/2004 | Graf et al. |
| 2004/0210199 A1 | 10/2004 | Atterbury et al. |
| 2004/0236282 A1 | 11/2004 | Braithwaite |
| 2004/0248782 A1 | 12/2004 | Bridon et al. |
| 2004/0249348 A1 | 12/2004 | Wimpenny et al. |
| 2004/0260247 A1 | 12/2004 | Veasey et al. |
| 2004/0267207 A1 | 12/2004 | Veasey et al. |
| 2005/0004529 A1 | 1/2005 | Veasey et al. |
| 2005/0009742 A1 | 1/2005 | Bertilsson et al. |
| 2005/0019400 A1 | 1/2005 | Deveney et al. |
| 2005/0033244 A1 | 2/2005 | Veasey et al. |
| 2005/0055011 A1 | 3/2005 | Enggaard |
| 2005/0143303 A1 | 6/2005 | Quay et al. |
| 2005/0148497 A1 | 7/2005 | Khan |
| 2005/0205083 A1 | 9/2005 | Staniforth et al. |
| 2005/0268915 A1 | 12/2005 | Wassenaar et al. |
| 2006/0084605 A1 | 4/2006 | Engelund et al. |
| 2006/0178304 A1 | 8/2006 | Juul-Mortensen et al. |
| 2006/0198896 A1 | 9/2006 | Liversidge et al. |
| 2006/0286129 A1 | 12/2006 | Sarubbi |
| 2006/0287221 A1 | 12/2006 | Knudsen et al. |
| 2007/0093761 A1 | 4/2007 | Veasey et al. |
| 2008/0125361 A1 | 5/2008 | Ludvigsen et al. |
| 2008/0293814 A1 | 11/2008 | Tiwari et al. |
| 2009/0011976 A1 | 1/2009 | Ludvigsen et al. |
| 2009/0156478 A1 * | 6/2009 | Lau .......... A61P 3/08 530/308 |
| 2010/0311643 A1 | 12/2010 | Bevec et al. |
| 2012/0208755 A1 | 8/2012 | Leung |
| 2012/0225810 A1 | 9/2012 | Pedersen et al. |
| 2013/0190230 A1 | 7/2013 | Casadesus Smith et al. |
| 2014/0187635 A1 | 7/2014 | Patel et al. |
| 2015/0011462 A1 | 1/2015 | Reedtz-Runge et al. |
| 2016/0235855 A1 | 8/2016 | Xiong et al. |
| 2019/0231876 A1 | 8/2019 | Pedersen et al. |
| 2019/0388502 A1 | 12/2019 | Corvari et al. |
| 2020/0316204 A1 | 10/2020 | Pedersen et al. |
| 2021/0050085 A1 | 2/2021 | Hayter et al. |
| 2021/0252111 A1 | 8/2021 | Engelund et al. |
| 2021/0379159 A1 | 12/2021 | Engelund et al. |

FOREIGN PATENT DOCUMENTS

| | | |
|---|---|---|
| CA | 2306024 | 4/1999 |
| CA | 2359375 A1 | 7/2000 |
| CA | 2527743 | 12/2004 |
| CA | 2960334 A1 | 4/2016 |
| CL | 2021001430 A1 | 11/2021 |
| CN | 1199339 A | 11/1998 |
| CN | 1250370 A | 4/2000 |
| CN | 1257510 A | 6/2000 |
| CN | 1376166 A | 10/2002 |
| CN | 101663022 A | 3/2010 |
| CN | 102579350 A | 7/2012 |
| CN | 105963257 A | 9/2016 |
| CN | 106999602 A | 8/2017 |
| CN | 105777872 | 6/2019 |
| DE | 3546150 | 1/1987 |
| DE | 3609555 A1 | 9/1987 |
| DE | 3900926 A1 | 8/1989 |
| DE | 42 08 677 A1 | 9/1993 |
| DK | 200101010 | 6/2001 |
| DK | 1412384 T3 | 4/2008 |
| EP | 0037043 B1 | 11/1984 |
| EP | 295075 | 12/1988 |
| EP | 0299527 A1 | 1/1989 |
| EP | 327910 | 8/1989 |
| EP | 359070 A2 | 3/1990 |
| EP | 0431679 | 11/1990 |
| EP | 0438767 | 12/1990 |
| EP | 450905 A1 | 10/1991 |
| EP | 0452281 A1 | 10/1991 |
| EP | 0496141 A1 | 7/1992 |
| EP | 498737 | 8/1992 |
| EP | 879610 | 8/1992 |
| EP | 608343 | 4/1993 |
| EP | 0552996 A1 | 7/1993 |
| EP | 0554996 | 8/1993 |
| EP | 594349 | 4/1994 |
| EP | 699687 | 8/1995 |
| EP | 0673482 | 9/1995 |
| EP | 699686 A2 | 3/1996 |
| EP | 702970 | 3/1996 |
| EP | 0708179 A2 | 4/1996 |
| EP | 747390 | 12/1996 |
| EP | 0923159 A2 | 6/1999 |
| EP | 0923950 A2 | 6/1999 |

(56) References Cited

FOREIGN PATENT DOCUMENTS

| | | |
|---|---|---|
| EP | 0926159 | 6/1999 |
| EP | 0926159 A2 | 6/1999 |
| EP | 0937471 | 8/1999 |
| EP | 937476 | 8/1999 |
| EP | 1003581 | 8/1999 |
| EP | 0978565 A1 | 2/2000 |
| EP | 1025125 A1 | 8/2000 |
| EP | 1329462 | 10/2001 |
| EP | 1424077 | 5/2002 |
| EP | 1250167 A1 | 10/2002 |
| EP | 1344533 | 9/2003 |
| EP | 1396499 | 3/2004 |
| EP | 1412384 A2 | 4/2004 |
| EP | 722492 | 3/2005 |
| EP | 1570876 A2 | 9/2005 |
| EP | 1601396 A2 | 12/2005 |
| EP | 1687019 A2 | 8/2006 |
| EP | 0944648 B1 | 3/2007 |
| EP | 2394656 A2 | 12/2011 |
| EP | 3295952 A1 | 3/2018 |
| FR | 2583291 | 12/1986 |
| FR | 2767479 | 2/1999 |
| GB | 735443 A | 8/1955 |
| GB | 995065 A | 6/1965 |
| GB | 1232899 A | 5/1971 |
| GB | 2141799 A | 1/1985 |
| HU | 213691 B | 9/1997 |
| HU | 215007 B | 8/1998 |
| HU | 215366 B | 12/1998 |
| HU | 215634 B | 1/1999 |
| IT | 1222331 B | 9/1990 |
| JP | H05337179 A | 12/1993 |
| JP | H06296691 A | 10/1994 |
| JP | 10101696 | 4/1998 |
| JP | 2000-510813 | 8/2000 |
| JP | 2001-525371 | 12/2001 |
| JP | 2002501790 A | 1/2002 |
| JP | 2002-504908 | 2/2002 |
| JP | 2002-508332 | 3/2002 |
| JP | 2002-524514 | 8/2002 |
| JP | 2002532557 A | 10/2002 |
| JP | 2003519195 | 6/2003 |
| JP | 3503129 B2 | 3/2004 |
| JP | 2004-518756 A | 6/2004 |
| JP | 2008530134 A | 8/2008 |
| JP | 2010528000 A | 8/2010 |
| JP | 2014520893 A | 8/2014 |
| JP | 2015522573 A | 8/2015 |
| JP | 2016508139 A | 3/2016 |
| KR | 20060135661 A | 12/2006 |
| KR | 20140018798 A | 2/2014 |
| KR | 20170021313 A | 2/2017 |
| PA | 200101010 | 6/2001 |
| RU | 2111019 | 5/1997 |
| RU | 2180218 | 3/2002 |
| TW | 267945 B | 1/1996 |
| WO | 87/06941 A1 | 11/1987 |
| WO | 8907463 | 8/1989 |
| WO | 9000200 | 1/1990 |
| WO | 90/09202 | 8/1990 |
| WO | 9010020 A1 | 9/1990 |
| WO | 90/11296 A1 | 10/1990 |
| WO | 9110460 A1 | 7/1991 |
| WO | 91/11457 A1 | 8/1991 |
| WO | 91/14467 A1 | 10/1991 |
| WO | 9217482 A1 | 10/1992 |
| WO | 9219260 | 11/1992 |
| WO | 9307922 | 4/1993 |
| WO | 9318785 | 9/1993 |
| WO | 9319175 A1 | 9/1993 |
| WO | 9323010 | 11/1993 |
| WO | 199325579 A1 | 12/1993 |
| WO | 94/15120 A1 | 7/1994 |
| WO | 9415120 | 7/1994 |
| WO | 94/19034 A1 | 9/1994 |
| WO | 9522560 | 2/1995 |
| WO | 95/07931 A1 | 3/1995 |
| WO | 9505848 | 3/1995 |
| WO | 9510605 | 4/1995 |
| WO | 9513825 | 5/1995 |
| WO | 95/31214 A1 | 11/1995 |
| WO | 9620005 | 7/1996 |
| WO | 9624369 | 8/1996 |
| WO | 96/29342 | 9/1996 |
| WO | 96/29344 | 9/1996 |
| WO | 9626754 A2 | 9/1996 |
| WO | 96/38190 A1 | 12/1996 |
| WO | 9638469 | 12/1996 |
| WO | 9736626 | 10/1997 |
| WO | 98/00152 A1 | 1/1998 |
| WO | 98005351 A1 | 2/1998 |
| WO | 98/08531 A1 | 3/1998 |
| WO | 98/08873 A1 | 3/1998 |
| WO | 9808871 | 3/1998 |
| WO | 9810813 | 3/1998 |
| WO | 98/19698 A1 | 5/1998 |
| WO | 9824767 A1 | 6/1998 |
| WO | 9831386 | 7/1998 |
| WO | 98030231 A1 | 7/1998 |
| WO | 98/43658 A1 | 10/1998 |
| WO | 9850059 A1 | 11/1998 |
| WO | 98/55144 A1 | 12/1998 |
| WO | 98/57688 A1 | 12/1998 |
| WO | 9856406 | 12/1998 |
| WO | 9856436 | 12/1998 |
| WO | 9916417 | 4/1999 |
| WO | 9916487 | 4/1999 |
| WO | 99/21888 A1 | 5/1999 |
| WO | 9921888 | 5/1999 |
| WO | 9921889 | 5/1999 |
| WO | 9929336 | 6/1999 |
| WO | 9929337 A1 | 6/1999 |
| WO | 9930731 | 6/1999 |
| WO | 99/34764 A2 | 7/1999 |
| WO | 9934822 A1 | 7/1999 |
| WO | 99/40788 A1 | 8/1999 |
| WO | 99/40928 A1 | 8/1999 |
| WO | 9938554 | 8/1999 |
| WO | 99/43341 | 9/1999 |
| WO | 99/43705 A1 | 9/1999 |
| WO | 99/43706 | 9/1999 |
| WO | 99/43708 | 9/1999 |
| WO | 99/47160 A1 | 9/1999 |
| WO | 9943707 | 9/1999 |
| WO | 0015224 A1 | 3/2000 |
| WO | 0037098 A1 | 6/2000 |
| WO | 00/41546 A2 | 7/2000 |
| WO | 0041546 | 7/2000 |
| WO | 00/55119 | 9/2000 |
| WO | 0062847 A1 | 10/2000 |
| WO | 0069413 A1 | 11/2000 |
| WO | 200073331 A2 | 12/2000 |
| WO | 01/04156 | 1/2001 |
| WO | 0100223 | 1/2001 |
| WO | 0101774 A1 | 1/2001 |
| WO | 0102369 A2 | 1/2001 |
| WO | 0104156 A1 | 1/2001 |
| WO | 01/10484 | 2/2001 |
| WO | 0119434 A1 | 3/2001 |
| WO | 01021198 A1 | 3/2001 |
| WO | 0143762 | 6/2001 |
| WO | 0149314 | 7/2001 |
| WO | 0149314 A2 | 7/2001 |
| WO | 0151071 | 7/2001 |
| WO | 0152937 | 7/2001 |
| WO | 0155213 | 8/2001 |
| WO | 0177141 | 10/2001 |
| WO | 01/98331 | 12/2001 |
| WO | 02067989 | 1/2002 |
| WO | 02/046227 | 6/2002 |
| WO | 0247715 | 6/2002 |
| WO | 0247716 | 6/2002 |
| WO | 0248183 | 6/2002 |
| WO | 02069994 A2 | 9/2002 |

(56) References Cited

FOREIGN PATENT DOCUMENTS

| | | |
|---|---|---|
| WO | 02069994 A3 | 9/2002 |
| WO | 2002098445 | 12/2002 |
| WO | 03002136 A2 | 1/2003 |
| WO | 2003002136 A2 | 1/2003 |
| WO | 03013589 | 2/2003 |
| WO | 03020201 | 3/2003 |
| WO | 03033671 A2 | 4/2003 |
| WO | 03035099 | 5/2003 |
| WO | 03/072195 A2 | 9/2003 |
| WO | 03084563 A1 | 10/2003 |
| WO | 03/101395 A2 | 12/2003 |
| WO | 2004004781 | 1/2004 |
| WO | 2004029076 | 4/2004 |
| WO | 04/037168 A2 | 5/2004 |
| WO | 04056313 A2 | 7/2004 |
| WO | 2004/078226 | 9/2004 |
| WO | 2004078226 A2 | 9/2004 |
| WO | 2004105781 | 12/2004 |
| WO | 2005000222 | 1/2005 |
| WO | 05/027978 A2 | 3/2005 |
| WO | 2005018721 A1 | 3/2005 |
| WO | 2005021026 A2 | 3/2005 |
| WO | 2005/046716 | 5/2005 |
| WO | 2005042488 | 5/2005 |
| WO | 2005044294 | 5/2005 |
| WO | 2005/058252 A2 | 6/2005 |
| WO | 2005049061 A2 | 6/2005 |
| WO | 2005081711 | 9/2005 |
| WO | 05120492 A1 | 12/2005 |
| WO | 2005113008 A1 | 12/2005 |
| WO | 06000567 A2 | 1/2006 |
| WO | 2006025882 | 3/2006 |
| WO | 2006052608 A2 | 5/2006 |
| WO | 2006055603 | 5/2006 |
| WO | 2006072065 | 7/2006 |
| WO | 2006076921 A1 | 7/2006 |
| WO | 2006/083254 A1 | 8/2006 |
| WO | 2006096461 | 9/2006 |
| WO | 2006097537 A2 | 9/2006 |
| WO | 2006099561 | 9/2006 |
| WO | 2007014051 A2 | 2/2007 |
| WO | 2007022518 A2 | 2/2007 |
| WO | 2007075720 | 7/2007 |
| WO | 2007094893 | 8/2007 |
| WO | 2007/120899 A2 | 10/2007 |
| WO | 2008011446 A2 | 1/2008 |
| WO | 2008019115 | 2/2008 |
| WO | 08133908 A2 | 11/2008 |
| WO | 09030771 A1 | 3/2009 |
| WO | 2009051992 | 4/2009 |
| WO | 2009064298 A1 | 5/2009 |
| WO | 2009075859 A2 | 6/2009 |
| WO | 2010/046357 A1 | 4/2010 |
| WO | 2010/107874 A2 | 9/2010 |
| WO | 2010/139793 A1 | 12/2010 |
| WO | 11050008 A2 | 4/2011 |
| WO | 11073328 A1 | 6/2011 |
| WO | 2011069629 | 6/2011 |
| WO | 2011/117415 A1 | 9/2011 |
| WO | 2011104378 A1 | 9/2011 |
| WO | 2011109784 A1 | 9/2011 |
| WO | 2011109787 A1 | 9/2011 |
| WO | 2012062803 A1 | 5/2012 |
| WO | 2012080471 A1 | 6/2012 |
| WO | 2012098187 A1 | 7/2012 |
| WO | 2012098188 A1 | 7/2012 |
| WO | 2012104655 A2 | 8/2012 |
| WO | 2012107476 A1 | 8/2012 |
| WO | 2012112626 A2 | 8/2012 |
| WO | 2012140117 A1 | 10/2012 |
| WO | 2012140155 A1 | 10/2012 |
| WO | 2012151248 | 11/2012 |
| WO | 2012168430 A2 | 12/2012 |
| WO | 2012168432 A1 | 12/2012 |
| WO | 2013009539 A1 | 1/2013 |
| WO | 2013/037690 A1 | 3/2013 |
| WO | 2013072406 | 5/2013 |
| WO | 13083826 A2 | 6/2013 |
| WO | 13127779 A1 | 9/2013 |
| WO | 2013139694 A1 | 9/2013 |
| WO | 2013151663 | 10/2013 |
| WO | 2013151668 | 10/2013 |
| WO | 2013151729 A1 | 10/2013 |
| WO | 2013156594 A1 | 10/2013 |
| WO | 2013/167454 A1 | 11/2013 |
| WO | 2013/167455 A1 | 11/2013 |
| WO | 2013177565 A1 | 11/2013 |
| WO | 2013190384 | 12/2013 |
| WO | 2014005858 A1 | 1/2014 |
| WO | 2014010586 A1 | 1/2014 |
| WO | 2014060472 A1 | 4/2014 |
| WO | 14144842 A2 | 9/2014 |
| WO | 2014177683 A1 | 11/2014 |
| WO | 2014182950 | 11/2014 |
| WO | 2014202780 | 12/2014 |
| WO | 2015000942 A1 | 1/2015 |
| WO | 2015009616 | 1/2015 |
| WO | 2015022400 A1 | 2/2015 |
| WO | 2015071355 A1 | 5/2015 |
| WO | 2015155151 A1 | 10/2015 |
| WO | 15200324 A1 | 12/2015 |
| WO | 2016001862 | 1/2016 |
| WO | 2016038521 A1 | 3/2016 |
| WO | 2016111971 A1 | 7/2016 |
| WO | 2017009236 A2 | 1/2017 |
| WO | 2017149070 A1 | 9/2017 |
| WO | 2017186896 A1 | 11/2017 |
| WO | 2018055539 A1 | 3/2018 |
| WO | 18096460 A1 | 5/2018 |
| WO | 18115901 A1 | 6/2018 |
| WO | 2018115901 A1 | 6/2018 |
| WO | 18139991 A1 | 8/2018 |
| WO | 2019038412 A1 | 2/2019 |
| WO | 2019122109 | 6/2019 |
| WO | 2020004368 A1 | 1/2020 |

OTHER PUBLICATIONS

Bailey et al. The Kinetics of Enzyme-Catalysed Reactions Biochemical Engineering Fundamentals, 2nd Ed., pp. 129-148 (1986).

Blundell, T.L., Handbook of Experimental Pharmacology, Chapter 3, "The Conformation of Glucagon", Springer Verlag, 1983, pp. 37-55.

Brittain, Harry G., Buffers, Buffering Agents, and Ionic Equilibria, Encyclopedia of Pharmaceutical Technology, p. 385, 2007.

Chou, J. Z. et al., Journal of Pharmaceutical Sciences, a Radioimmunoassay for LY315902, an Analog of Glucagon-Like Insulinotropic Pepride, and Its Application in the Study of Canine Pharmacokinetics, vol. 86(7), pp. 768-773 (1997).

D. Voet and J.G. Voet, "Abnormal Hemoglobins", Biochem, 2nd Ed., pp. 235-241 (1995).

D.E. Smilek et al., "A Single Amino Acid Change in a Myelin Basic Protein Peptide Confers the Capacity to Prevent Rather Than Induce Experimental Autoimmune Encephalomyelitis", Proc Natl Acad Sci USA, vol. 88, pp. 9633-9637, (1991).

Eli Lilly & Co., Humalog Lispro Injection, USP Product Information Dated Feb. 11, 2010.

Entry for Glycerin in Drugs.com (www.drugs.com/ppa/glycerin-glycerol.html), printed Aug. 4, 2009.

European Pharmacopoeia, 3RD Edition, 2.2.3, 1997, pp. 17-18, Council of Europe-Strasbourg.

European Pharmacopoeia, 2007, vol. 1, p. 730, Council of Europe-Strasbourg.

Frokjaer & Hovgaard, Pharmaceutical Formulation Development of Peptides and Proteins, Chapter 8, "Peptides and Proteins as Parenteral Solutions", 2000, pp. 145-148 & 150-151.

Further Experimental Data, Part A, Physical Stability, Dated Jun. 22, 2009.

G.F. Stamper et al., "Accelerated Stability Testing of Proteins and Peptides: pH-Stability Profile of Insulinotropin Using Traditional

(56) References Cited

OTHER PUBLICATIONS

Arrheneius and Non-Linear Fitting Analysis", Drug Development and Industrial Pharmacy, 1995, vol. 21, No. 13, pp. 1503-1511.
Gonzales, Johnny C., Declaration of (Including Curriculum Vita) Dated Nov. 1, 2010.
H. Qi et al., "Stability and Stabilization of Insulinotropin in a Dextran Formulation", PDA Journal of Pharmaceutical Science & Technology, vol. 49, No. 6, Nov.-Dec. 1995, pp. 289-293.
H.J.C. Berendsen, a Glimpse of the Holy Grail, Science, vol. 282, pp. 642-643 (1998).
Knudsen, L.B. et al., Potent Derivatives of Glucogon-Like Peptide-1, Journal of Medicinal Chemistry, 2000, vol. 43, pp. 1664-1669.
Kristensen, H.G., Almen Farmaci, 2000, pp. 273-274, 281.
Larsen, P.J. et al., "Systemic Administration of the Long Acting Glp-1 Derivative NN2211 Induces Lasting and Reversible Weight Loss in Both Normal and Obese Rats", Diabetes, 2001, vol. 50, pp. 2530-2539.
Lund, Walter, Editor, the Pharmaceutical Codex, 12th Edition, Principles and Practice of Pharmaceutics, 1994, the Pharmaceutical Press, London, pp. 98-99.
Malendowicz, L.K. et al., "Preproglucagon derived peptides and thyrotropin (TSH) secretion in the rat: Robust and sustained lowering of blood TSH levels in extendin-4 injected animals", International Journal of Molecular Medicine, vol. 10, pp. 327-331 (2002).
Mack Publishing Co., Remington's Pharmaceutical Sciences, 16th Edition, 1980, Chapter 79, p. 1406.
Mack Publishing Co., Remington's Pharmaceutical Sciences, 18th Edition, 1990, Chapter 84 "Parental Preparations", pp. 1545-1550.
Martin A. et al., Physical Pharmacy; Physical Chemical Principles in the Pharmaceutical Sciences, 1983, 3rd Edition, p. 222-225.
N. Good et al., "Hydrogen Ion Buffers for Biological Research", Biochemistry, 1966, vol. 5, No. 2, pp. 467-477.
Rudinger, In: "Characteristics of the Amino Acids as Components of a Peptide Hormone Sequence", Peptide Hormones, JA Parsons, Ed., pp. 1-7 (1976).
S.E. Bondos & A. Bicknell, Detection and prevention of protein aggregation before during and after purification, Analytical Biochemistry, 2003, 223-231, vol. 316, Academic Press.
Senderoff, R.I. et al., Consideration of Conformational Transitions and Racemization during Process Development of Recombinant Glucagon-like Peptide-1, Journal of Pharmaceutical Sciences, 1998, 183-189, vol. 87—No. 2, American Chemical Society & American Pharm. Assc.
Sigma Product Information on Gly-Gly Buffer Dated Mar. 16, 2010.
Sigma, "Designing Custom Peptides" http://www.sigma-genosys.com/peptidedesign.asp (accessed Dec. 16, 2004).
Singh, S. et al., "Effect of Polyols on the Conformational Stability and Biological Activity of a Model Protein Lysozyme", AAPS Pharmscitech, vol. 4(3), pp. 334-342 (2003).
Skovgaard et al., "Using Evolutionary Information and Ancestral Sequences to Understand the Sequence-Function Relationship in GLP-1 Agonists," J. Mol. Bio., 2006, vol. 363, pp. 977-988.
Stenesh, J. "Foundation of Biochemistry—Biomolecules", Biochemistry, 1998, pp. 67-69.
Tsoka et al., Selective Flocculation ands Precipitation for the Improvement of Virus-Like Particle Recovery From Yeast Homogenate, Biotechnol Prog. vol. 16(4), pp. 661-667 (2000).
United States Pharmacopoeia, 24th Edition, 1999, pp. 1977-1978.
Villanueva_Penacarril, M.L., Potent Glycognic Effect of GLP-1(7-36) Amide in Rat Skeletal Muscle, Diabetologia, 1994, vol. 37, pp. 1163-1166.
Wang & Hansen, "Parenteral Formulations of Proteins and Peptides: Stability and Stabilizers", Journal of Parenteral Science & Technology, 1988, vol. 42, pp. 4-26.
Wang et al., Aggregation of Therapeutic Proteins, 2010, p. 241.
Weinstein, Sharon, "Principles of Parenteral Fluid Administration", Plumer's Principles & Practice of Intravenous, 2006, vol. 8 (8), pp. 124-128.

W.S. Messer, Vasopressin and Oxytocin,, Apr. 3, 2000, http://www.neurosci.pharm.utoldeo.edu/MBC3320/vasopressin.htm.
Duma et al., Pharmaceutical Dosage Forms: Parenteral Medications, 1991, vol. 1, 2nd Edition, p. 20.
http://www.copewithcytokines.de/cope.cgi?key=insulinotropin; (Host Ibelgauft's COPE: Cytokines & Cells Online pathfinder Encyclopedia; insulinotropin), 1987.
http://www.copewithcytokineslde/cope.cgi?key=GLP%2dl; (Host Ibelgauft's COPE: Cytokines & Cells Online Pathfinder Encyclopedia; GLP-1), 1987.
http://www.fermantas.com/techinfo/appendix/appendixtables1.htm, 'Temperature Dependence of the Ph for Commonly Used Buffers' + 'Temperature Dependence of the Ph of 50 MM TRIS-HCL Solutions', 1966.
http://www.sigmaaldrich.com/life-science/metabolomics/enzyme-explorer/learning-center/assay-library/assays-by-enzyme-name-ii.html#%20G%, Enzymatic Assay of Glucose-6-Phosphate obtained from the Sigma Aldrich website, 1996.
Pridal et al., "Absorption of Glucagon-Like PEPTIDE-1 Can Be Protracted By Zinc or Protamine", International Journal of Pharmaceutics, 1996, vol. 136, pp. 53-59.
Ruzin, 1999, Plant Microtechnique and Microscopy, "Buffers", Accessed On-Line on Dec. 24, 2013 at http://microscopy.berkeley.edu/resources/instruction/bufers.html, pp. 1-6.
Native Luteinizing Hormone-Releasing Hormone (LHRH) and Hydrophobic Analogues in Aqueous Solution, Journal : Pharmaceutical Research, Year 1991, vol. 8. No. 10 pp. 1258-1263.
Powell Micheal F. et al.Parenteral Peptide Formulations:Chemical and Physical hoperties of Native Luteinizing Hormone-Releasing Hormone (LHRH) and Hydrophobic Analogues in Aqueous Solution, Journal :Pharmaceutical Research, Year 1991, vol. 8. No. 10 pp. 1258-1263.
Powell Micheal F. et al.Parenteral Peptide Formulations:Chemical and Physical properties of Native Luteinizing Hormone-Releasing Hormone (LHRH) and Hydrophobic Analogues in Aqueous Solution, Journal :Pharmaceutical Research, Year 1991, vol. 8. No. 10 pp. 1258-1263.
Letter dated Jul. 8, 2011 submitted in response to the First Examination Report during prosecution of the impugned Patent application.
"Parenteral Preparations"Remington, Joseph Price. Remington: the science and practice of pharmacy. Eds. Alfonso R Gennaro, vol. 1.Lippincott Williarns & Wilkins, 20th edition, 2000, Chapter 41, pp. 780-785.
INPADOC patent family for WO2005049061 as downloaded from worldwide.espacenet.com, last updated Jun. 11, 2014.
Ranbaxy Opposition dated Sep. 29, 2014.
Post-grant Opposition filed by Ranbaxy in relation to Indian patent No. 257402, dated Sep. 29, 2014.
Post Grant Opposition filed USV Limited in relation to Indian patent No. 257402, dated Sep. 26, 2014.
Post-grant Opposition filed by Ranbaxy Laboratories Limited in relation to Indian patent No. 257402, dated Sep. 29, 2014.
Product Insert Victoza, 2012.
Rejection Decision of the chinese application CN201210294716.8 as a divisional application of the present patent, dated Dec. 2, 2014.
Chinese translations of the cited portions in evidence 1 (WO03002136—cited Oct. 12, 2012) and evidence 2 (WO9522560—cited Oct. 12, 2012).
Affidavit of Omar Sherief Mohammad submitted in Ranbaxy Opposition dated Jul. 7, 2015.
International Diabetes Federation. IDF diabetes atlas. 6th ed. http://www.idf.org/diabetesatlas. Published 2013. Accessed Feb. 12, 2014.
Hex N, et al., Estimating the current and future costs of type 1 and type 2 diabetes in the UK, including direct health costs and indirect societal and productivity costs. Diabetic Medicine. 2012, vol. 29 No. 7, pp. 855-862.
Stratton IM et al., on behalf of the UK Prospective Diabetes Study Group. Association of glycaemia with macrovascular and microvascular complications of type 2 diabetes (UKPDS 35): prospective observational study. BMJ, 2000, vol. 321 No. 7528, pp. 405-412.

(56) References Cited

OTHER PUBLICATIONS

Villareal DT, et al., Weight loss therapy improves pancreatic endocrine function in obese older adults, Obesity, 2008, vol. 16, No. 6 pp. 1349-1354.
Bron M, et al.. Hypoglycemia, treatment discontinuation, and costs in patients with type 2 diabetes mellitus on oral antidiabetic drugs, Postgraduate Medicine, 2012, vol. 124, No. 1, pp. 124-132.
Zinman B, et al., Achieving a clinically relevant composite outcome of an HbA1C of less than 7% without weight gain or hypoglycaemia in type 2 diabetes: a meta-analysis of the liraglutide clinical trial programme, Diabetes, Obesity and Metabolisim, 2012, vol. 14, No. 1, pp. 77-82.
Garber A et al., for the LEAD-3 (Mono) Study Group. Liraglutide versus glimepiride monotherapy for type 2 diabetes (LEAD-3 Mono): a randomised, 52 week, phase III, double-blind, parallel-treatment trial. Lancet. 2009, vol. 373, No. 9662, pp. 473-481.
Valentine WJ, et al., Evaluating the long-term cost-effectiveness of liraglutide versus exenatide BID in patients with type 2 diabetes who fail to improve with oral antidiabetic agents, Clinical Therapeutics, 2011, vol. 33, No. 11, pp. 1698-1712.
International Diabetes Federation. IDF diabetes atlas. 5th ed. http://www.idf.org/sites/default/files/da5/5eDiabetesAtlas_2011.pdf. Published 2011. Accessed Dec. 20, 2013.
Blundell, T.L, Lefébvre P.J (Ed), "The Conformation of Glucagon", 1983, vol. 66, pp. 37-55.
Senderoff, Journal of Pharmaceutical Sciences, "Consideration of Conformational Transitions and . . . ", 1998, vol. 87, No. 2, pp. 183-189.
D. Voet and J.G. Voet, Biochem, 2nd Ed., pp. 235-241 (1995).
D.E. Smilek et al., Proc Natl Acad Sci USA, vol. 88, pp. 9633-9637, (1991).
Larsen, P.J. et al., Systemic Administration of the Logn Acting GLP-1, Diabetes, 2000 vol. 50, pp. 2530-2539.
Rudinger, In: Peptide Hormones, JA Parsons, Ed., pp. 1-7 (1976).
Sigma, http://www.sigma-genosys.com/peptide design.asp (accessed Dec. 16, 2004).
Singh, S. et al. AAPS Pharmscitech, vol. 4(3), pp. 334-342 (2003).
Duma et al., Pharmaceutical Dosage Forms: Parenteral Medications, vol. 1, 2nd Edition, p. 20, 1992.
Eli Lilly & Co., Humalog Lispro Injection, USP Product Information dated Nov. 2, 2010.
European Pharmacopoeia, 3rd Edition, 2.2.3, 1997, pp. 17-18, Council of Europe-Strasbourg, "Physical and Physiochemical Methods".
Declaration of Johnny C. Gonzalez, (Including Curriculum Vita) dated Nov. 1, 2010.
Knudsen, L.B. et al., Journal of Medicinal Chemistry, 2000, vol. 43, pp. 1664-1669, "Potent Derivatives of Glucagon-like Peptide-1 with Pharmacokinetic Properties Suitable for Once Daily Administration".
Kristensen, H.G., Almen Farmaci, 2000, pp. 273-274, 281, "Parenteral Administration".
Lund, Walter, Editor, the Pharmaceutical Codex, 12th Edition, 1994, The Pharmaceutical Press, London, pp. 98-99, "Principles and Practice of Pharmaceutics".
Mack Publishing Co., Remington's Pharmaceutical Sciences, 16th Edition, 1980, PT. 79, p. 1406, "Undesirable Effects of Abnormal Osmoticity".
Martin A. et al., Physical Pharmacy, 1983, 3rd Edition, p. 232, "Physical Chemical Principles in the Pharmaceutical Sciences".
Sigma Product Information on Gly-Gly Buffer Mar. 16, 2010.
United States Pharmacopoeia, 24th Edition, 1999, pp. 1977-1978, "Polarography—Physical Tests".
Weinstein, Sharon, Plumer's Principles & Practice of Intravenous, 2006, vol. 8 (8), pp. 124-128, "Principles of Parenteral Fluid Administration".
Brittain, Harry G., Buffers, Buffering Agents, and Ionic Equilibria, Encyclopedia of Pharmaceutical Technology, p. 385, 2007.
Greig et al. Once daily injection of exendin-4 to diabetic mice achieves long-term beneficial effects on blood glucose concentrations,Diabetologia, 1999, vol. 42 pp. 45-50.
U.S. Appl. No. 60/036,226, filed Jan. 24, 1997.
U.S. Appl. No. 60/036,255, filed Jan. 24, 1997.
U.S. Appl. No. 60/082,478, filed Apr. 21, 1998.
U.S. Appl. No. 60/082,480, filed Apr. 21, 1998.
Ven de Weert & Randolph, "Physical Instability of Peptides and Proteins", in Pharmaceutical Formulation Development of Peptides and Proteins, 2nd Ed, 2013, pp. 107-116 & 119-126.
Wolffenbuttel et al., "New Treatments for Patients with Type 2 Diabetes Mellitus", Postgrad Med J., Nov. 1996, vol. 72, No. 853, pp. 657-662.
Norditropin® Approved Labeling (revised May 2000).
Kibbe, Handbook of Pharmaceutical Excipients, 2000, 3rd Edition, American Pharmaceutical Association, Washington, DC, all pp. 220-222, 324-328, 442-444, 493-495, 496-497.
Handbook of Pharmaceutical Excipients (4th ed. 2003) pp. 257-259; 373-377; 521-523; 574-578.
Remington's Pharmaceutical Sciences (18th ed. 1990) Chs. 16-17, pp. 207-246; Ch. 19, pp. 257-309; Ch. 28, pp. 495-528; Chs. 35-38, pp. 697-773; Ch. 66, pp. 1286-1329; Ch. 69, pp. 1349-1364; Chs. 75-76, pp. 1435-1458; Ch. 79, pp. 1481-1498; Chs. 81-85, pp. 1504-1580; Ch. 87, pp. 1596-1614.
Remington's Pharmaceutical Sciences (19th ed. 1995) vol. II, pp. 843-1934.
UNC, Eshelman School of Pharmacy, The Pharmaceutics and Compounding Laboratory. "Sterile Compounding: Syringes and Needle," 1996, available online at https://pharmlabs.unc.edu/labs/parenterals/syringes.htm, pp. 1-2, accessed Nov. 30, 2020.
John Wiley & Sons, Inc., Common Buffers, Media, and Stock Solutions, in: Current Protocols in Human Genetics, Aug. 2000, Appendix 2D, vol. 26, No. 1, pp. 1-13.
Annexure A: Complete Specification of 6575/DELNP/2013 along with the as filed claims (1-47)) and amended claims (1-27), dated Jul. 23, 2018.
Annexure B: The original version and the machine translated version (Portuguese to English) of said Office actions, Denial decision, Appeal against the Denial decision and Appeal decision along with technical examination report with respect to Brazilian counterpart patent application BRP10416743A1.
Reich et al., "Tonicity, Osmoticity, Osmolality and Osmolarity," the Science and Pharmacy, 1995, vol. 1, No. 4, Chapter 36, pp. 613-627.
Hong Qi et al., "Stability and Stabilization of Insulinotropin in a Dextran Formulation," PDA Journal of Pharmaceutical Science and Technology, Pharmaceutical Research and Development, Pfizer Central Research, Nov.-Dec. 1995, vol. 49, No. 6, pp. 289-293.
Yang et al.,"The diabetes drug semaglutide reduces infarct size, inflammation, and apoptosis, and normalizes neurogenesis in a rat model stroke", Aug. 2019, Neuropharmacology,, vol. 158, No. 107748, pp. 1-14.
Doenicke et al. "Solvent for etomidate may cause pain and adverse effects." British journal of anaesthesia. Sep. 1999, vol. 83, No. 3, pp. 464-466.
Fransson et al., "Local Tolerance of Subcutaneous Injections," Journal of Pharm. Pharmacol., Oct. 1996, vol. 48, pp. 1012-1015.
Niedermirtl et al., "Etomidate and propylene glycol activate nociceptive TRP ion channels." Molecular pain. Nov. 2018, vol. 14, p. 1-18.
Marso et al., "Semaglutide and Cardiovascular Outcomes in Patients with Type 2 Diabetes", the New England Journal of Medicine, Sep. 16, 2016, vol. 375, No. 19, pp. 1834-1844.
Sorli et al., "Efficacy and safety of once-weekly semaglutide monotherapy versus placebo in patients with type 2 diabetes (Sustain 1): a double-blind, randomised, placebo-controlled, parallel-group, multinational, multicentre phase 3a trial", the Lancet Diabetes & Endocrinology, Apr. 2017, vol. 5, No. 4, pp. 251-260.
Shinotesuto, Patentabstracts of Japan, JP10101696, filed Apr. 21, 1998.
Shinotesuto, Patentabstracts of Japan, JP10101696, filed Apr. 21, 1997.
Rowe et al., "Handbook of Pharmaceutical Excipients", 2006, Fifth Edition, pp. 514-516.

(56) References Cited

OTHER PUBLICATIONS

Meyer et al., "Antimicrobial preservative use in parenteral products: Past and present," Jour Pharm Sci, Dec. 2007, vol. 96, No. 12, pp. 3155-3167.
Geier et al., "The relative toxicity of compounds used as preservatives in vaccines and biologics", Med Sci Monit, May 2010, vol. 16, No. 5, pp. SR21-27.
Luo Mingsheng et al., "The Extra Pharmaceutical Necessities", Sichuan Science and Technology, Mar. 31, 1993, p. 495.
Nauck, et al., "A Phase 2, Randomized, Dose-Finding Study of the Novel Once-Weekly Human GLP-1 Analog, Semaglutide, Compared With Placebo and Open-Label Liraglutide in Patients With Type 2 Diabetes", Diabetes Care, 2016, vol. 39, pp. 231-241.
Blundell et al., "Effects of once-weekly Semaglutide on appetite, energy intake, control of eating, food preference and body weight in subjects with obesity," Diabetes Obes Metab, 2017, vol. 19, pp. 1242-1251.
Bontempo, "Preformulation Development of Parenteral Biopharmaceuticals", Development of Biopharmaceutical Parenteral Dosage Forms, 1997, pp. 91-14.
Manandhar et al., "Glucagon-like peptide-1 (GLP-1) analogs: recent advances, new possibilities, and therapeutic implications." Journal of medicinal chemistry, Oct. 2014, vol. 58, No. 3, pp. 1020-1037.
Kapitza et al., "Semaglutide, a Once-Weekly Human GLP-1 Analog, Does Not Reduce the Bioavailability of the Combined Oral Contraceptive, Ethinylestradiol/Levonorgestrel," J Clin Pharmacol., May 2015, vol. 55, No. 5, pp. 497-504.
Patel et al., "Stability Considerations for Biopharmaceuticals: Overview of Protein and Peptide Degradation Pathways", Bioprocess International, Jan. 2011, pp. 1-22.
Gokarn et al., "Excipients for Protein Drugs", Excipient Development for Pharmaceutical, Biotechnology and Drug Delivery Systems, 2006, pp. 291-333.
Broadhead, "Parenteral Dosage Forms", Pharmaceutical Preformulation and Formulation a Practical Guide From Candidate Drug Selection to Commercial Dosage Form, 2007, pp. 331-354.
Akers et al., "Peptides and Proteins as Parenteral Solutions", Pharmaceutical Formulation Development of Peptides and Proteins, 2012, 2nd Edition, pp. 149-192.
Guidelines of regulatory authorities regarding the development of pharmaceutical preparations, Guidance for Industry Q8(R2) Pharmaceutical Development, Nov. 2009, pp. 1-33.
Gelhorn et al., "Evaluating preferences for profiles of GLP-1 receptor agonists among injection-naïve type 2 diabetes patients in the UK", Patient Prefer Adherence, Nov. 2015, vol. 9, pp. 1611-1622.
Bis et al., "Antimicrobial preservatives induce aggregation of interferon alpha-2a: the order in which preservatives induce protein aggregation is independent of the protein", Int J Pharm, Sep. 10, 2014, vol. 472, No. 1-2, pp. 356-361.
Regulatory guidelines regarding the use of preservatives, the European Agency for the Evaluation of Medicinal Products, 1997, 2003, 2007, pp. 1-27.
Set of Claims from Apr. 2021 and Applicant's accompanying letter.
Brunner and Suddarth's textbook of medical-surgical nursing, Seventh Edition, edited by Suzanne C. Smeltzer, Lippincott Company, 1992, pp. 1122-1123.
Cheng Qiao-yun, Discussion on the Safe Times of Repeated Uses of the Syringe Special for Insulin Injection at Home, Journal of Nursing (China), Nov. 2006, vol. 13 No. 11, pp. 87-89.
Fleming et al., Challenging Traditional Insulin Injection Practices, American Journal of Nursing, Feb. 1999, vol. 99(2), pp. 72-74.
Cooperative Multimodal Communication, edited by Harry Bunt, Springer, 2001, p. 17.
Cao Hongxia, Caring Guideline for application of Novolin by diabetes patient, Family Nurse, Feb. 2008, vol. 6 No. 2A, pp. 344-345.
United States Pharmacopeia and National Formulary (USPNF), United States Pharmacopeial Convention, 2003, pp. 2679-2682.
File History of European Patent No. EP1412384, filed Jun. 27, 2002.
Danish Patent App. No. PA199500275, filed Mar. 17, 1995.
Adelhorst, et al., "Structure-activity Studies of Glucagon-like Peptide-1," J. Bio. Chem. 269(9):6275-6278 (1994).
Akers, "Excipient-Drug Interactions in Parenteral Formulations," J. Pharm. Sci. 91:2283-2300 (2002).
Avis and Levchuk, "Parenteral Preparations," Chapter 87 in Remington's Pharmaceutical Sciences, 19th ed., vol. 2, pp. 1524-1548 (1995).
Bojesen and Bojesen, "Albumin Binding of Long-chain Fatty Acids: Thermodyanmics and Kinetics," J. Phys. Chem. 100(45):17981-17985 (1996).
Conlon, "Proglucagon-derived peptides: nomenclature, biosynthetic relationships and physiological roles," Diabetologia 31:563-566 (1988).
Cistola, et al., "Carbon 13 NMR Studies of Saturated Fatty Acids Bound to Bovine Serum Albumin," J. Biological Chem. 262(23):10980-10985 (1987).
Clodfelter et al., "Effects of non-covalent self-association on the subcutaneous absorption of a therapeutic peptide," Pharmaceutical Res. 15(2):254-262 (1998).
Deacon, et al., "Both Subcutaneously and Intravenously Administered Glucagon-Like Peptide I Are Rapidly Degraded From the NH2-Terminus in Type II Diabetic Patients and in Healthy Subjects," Diabetes 44:1126-1131 (1995).
Doenicke, et al., "Solvent for etomidate may cause pain and adverse effects," Br. J. Anaesth. 83(3):464-466 (1999).
Doenicke, et al., "Osmolalties of Propylene Glycol-Containing Drug Formulations for Parenteral Use. Should Propylene Glycol Be Used as a Solvent?" Anesth. Analg. 75:431-435, 431 (1992).
Klement and Arndt, "Pain on IV Injection of Some Anaesthetic Agents Is Evoked by the Unphysiological Osmolality or pH of Their Formulations," Br. J. Anaesth. 66:189-195 (1991).
Knudsen, et al., "GLP-1 derivatives as novel compounds for the treatment of type 2 diabetes: Selection of NN2211 for clinical development," Drugs of the Future 26(7): 677-685 (Jul. 2001).
Kurtzhals, et al., "Albumin binding of insulins acylated with fatty acids: characterization of the ligand-protein interaction and correlation between binding affinity and timing of the insulin effect in vivo," J. Biochem. 312: 725-731 (1995).
Lehninger, Biochemistry: the Molecular Basis of Cell Structure and Function, 2:72-76, 279-281 (1975).
Markussen, J. et al., "Soluble, Fatty Acid Acylated Insulins Bind to Albumin and Show Protracted Action in Pigs," Diabetologia 39:281-288 (1996).
Peters, T., "Ligand Binding by Albumin," All About Albumin, 76-95, Academic Press, Inc. (1995).
Radebaugh and Ravin, "Preformulation," Chapter 83 in Remington's Pharmaceutical Sciences, 19th ed. 2:1447-1462 (1995).
Ravin and Radebaugh, "Preformulation," Chapter 75 in Remington's Pharmaceutical Sciences, 18th ed. 1435-1450 (1990).
Sigma-Aldrich, Glycylglycine Product Information Sheet, Accessed online at https://www.sigmaaldrich.com/content/dam/sigma-aldrich/docs/Sigma/Product_Information_Sheet/g1002pis.pdf (last accessed Dec. 14, 2017).
Strickley, "Solubilizing Excipients in Oral and Injectable Formulations," Pharm. Research 21(2):201-230 (2004).
Stryer, "Protein Structure and Function," Biochemistry 4th ed.: 17-44 (1995).
Sweetana and Akers, "Solubility Principles and Practices for Parenteral Drug Dosage Form Development," PDA Journal of Pharmaceutical Science and Technology 50:330-342 (1996).
Thornton and Gorenstein, "Structure of Glucagon-like Peptide(7-36) Amide in a Dodecylphosphocholine Micelle as Determined by 2D NMR," Biochem. 33:3532-3539 (1994).
Toney, et al., "Aspartimide Formation in the Joining Peptide Sequence of Porcine and Mouse Proopiomelanocortin," J. Biol. Chem. 268(2):1024-1031 (1993).
Tonsgard, J. H. et al., "Binding of Straight-Chain Saturated Dicarboxylic Acids to Albumin," J. Clin. Invest. 82:1567-1573 (1988).
Wang and Hanson, "Parenteral Formulations of Proteins and Peptides: Stability and Stabilizers," Journal of Parenteral Science & Technology 42:S2-S36 (1988).

(56) References Cited

OTHER PUBLICATIONS

Whittingham, et al., "Crystal Structure of a Prolonged-Acting Insulin with Albumin-Binding Properties," Biochemistry 36:2826-2831 (1997).
Remington's Pharmaceutical Sciences, 19th ed., vol. 2:843-1934 (1995).
Siegel, "Tonicity, Osmoticity, Osmolality and Osmolarity," Chapter 79 in Remington's Pharmaceutical Sciences, 18th ed. :1481-1498 (1990).
Smyth and Evans, "Critical Analysis," Chapter 28 in Remington's Pharmaceutical Sciences, 18th ed. :495-528 (1990).
Vadas, "Stability of Pharmaceutical Products," Chapter 81 in Remington's Pharmaceutical Sciences, 18th ed. :1504-1512 (1990).
Turco, "Intravenous Admixtures," Chapter 85 in Remington's Pharmaceutical Sciences, 18th ed. :1570-1580 (1990).
Zografi and Schott, "Disperse Systems," Chapter 19 in Remington's Pharmaceutical Sciences, 18th ed. :257-309 (1990).
Reilly, "Pharmaceutical Necessities," Chapter 80 in Remington's Pharmaceutical Sciences, 18th ed. :1380-1416 (1990).
Selected Pages from Remington's Pharmaceutical Sciences :761-762, 1406, 1467 (1980).
Sokoloski, "Solutions and Phase Equilibria," Chapter 16 in Remington's Pharmaceutical Sciences, 18th ed. :207-227 (1990).
Swinyard and Lowenthol, "Pharmaceutical Necessities," Chapter 66 in Remington's Pharmaceutical Sciences, 18th ed. :1286-1329 (1990).
Selected Pages from Remington's Pharmaceutical Sciences, 18th ed. :266-269, 1302-1303, 1444-1445, 1448-1449, 1484-1485, 1506-1509, 1550-1551 (1990).
Yalkowsky, et al., "In Vitro Method for Detecting Precipitation of Parenteral Formulations After Injection," Journal of Pharmaceutical Sciences 72(9): 1014-1017 (1983).
Declaration of Johnny C. Gonzalez, Nov. 2010, pp. 1-7.
M. J. Reader, "Influence of Isotonic Agents on the Stability of Thimerosal in Ophthalmic Formulations," Journal of Pharmaceutical Sciences, 1984, vol. 73, pp. 840-841.
"Disodium Hydrogen Phosphate," PubChem CID: 24203, available online at https://pubchem.ncbi.nim.nih.gov/compound/disodium_hydrogen_phosphate#section=top, 72 pages (accessed on Jan. 10, 2018).
Catanzaro et al., "Propylene glycol dermatitis", Jan. 1991, Journal of the American Academy of Dermatology, vol. 24, No. 1, pp. 90-95.
Chi et al. "Physical stability of proteins in aqueous solution: mechanism and driving forces in nonnative protein aggregation." Pharmaceutical research, Sep. 2003, vol. 20, No. 9, pp. 1325-1336.
Cleland et al. "Formulation and delivery of proteins and peptides: design and development strategies." (1994), Chapter 1, pp. 1-19.
Contaxis et al."A study of the conformational properties of glucagon in the presence of glycols." Canadian journal of biochemistry, 1972, vol. 52, No. 6, pp. 456-468.
Frokjaer et al. "Protein drug stability: a formulation challenge." Nat Rev Drug Discov, Apr. 2005, vol. 4, No. 4, pp. 298-306.
Furia, Thomas., "CRC Handbook of Food Additives, 2nd Ed." (1972), vol. I, Chapter 10.
Goolcharran et al. "Chemical pathways of peptide and protein degradation." Pharmaceutical formulation and development of peptides and proteins, 2000, Chapter 5, pp. 70-88.
Gutniak, Mark et al. "Antidiabetogenic Effect of Glucagon-like Peptide-1 (7-36)amide in Normal Subjects and Patients with Diabetes Mellitus" the New England Journal of Medicine. May 1992. vol. 326(20) pp. 1316-1322. Oth.
Hashimoto M et al., Synthesis of palmitoyl derivatives of insulin and their biological activities, Pharmaceutical Research, Feb. 1989, vol. 6(2), 171-176, Others.
Humira® Package Insert (revised Jan. 2003) retrieved from https://www.accessdata.fda.gov/drugsatfda_docs/label/2002/adalabb123102lb.htm Accessed Nov. 12, 2020.
Japanese Pharmaceutical Excipients Directory (1996), at p. 437.

Jeffrey et al. "The Preparation of a Sterile Solution of Mannitol." American Journal of Hospital Pharmacy, May 1963, vol. 20, No. 5, pp. 255-258.
Kaiser et al., "Secondary structures of proteins and peptides in amphiphilic environments (a Review)" 80 Proc. Natl. Acad. Sci. USA, Feb. 1983, vol. 80, No. 4, pp. 1137-1143.
Kenyon et al., "13C NMR Studies of the Binding of Medium-Chain Fatty Acids to Human Serum Albumin", 35 J. Lipid Research, Mar. 1994, vol. 35, No. 3, pp. 458-467.
Kitsberg, "Not Quite Crystal Clear", Anaesthesia, Mar. 2002, vol. 57, No. 3, pp. 284-313.
Losasso et al., "Doppler Detection of Intravenous Mannitol Crystals Mimics Venous Air Embolism",, Anesth Analg, Nov. 1990, vol. 71, No. 5 , pp. 561-569.
Maniatis, T et al., Journal Title: Cold Spring Harbor Laborator, Title: Molecular Cloning a Laboratory Manual, 1982, pp. 324-328, AU Office Action.
Manning, M.C et al., Journal Title: Pharmaceutical Research, Stability of Protein Pharmaceuticals, 1989, vol. 6, No. 11, pp. 903-918,.
Meier, et al., "Contrasting Effects of Lixisenatide and Liragluide on Postprandial Glycemic Control, Gastric Emptying, and Safety Parameters in Patients with Type 2 Diabetes on Optimized Insulin Glargine with or Without Metformin: a Randomized, Open-Label Trial", Diabetes Care, Jul. 2015, vol. 38, No. 7, pp. 1263-1273.
Mentlein, R et al., "Dipeptidyl-peptidase IV hydrolyses gastric inhibitory polypeptide, glucagonlike peptide-1 (7-36) amide, peptide histidine methionine and is responsible for their degradation in human serum" 1993, European Journal of Biochemistry, vol. 214, pp. 829-835.
Nauck et al., JTitle: Normalization of Fasting Hyperglycemia by Exogenous Glucagon-Like Peptide 1 (7-36 Amide) in Type 2 (Non-Insulin-Dependent) Diabetic Patients, 1993, vol. 36, pp. 741-744.
Niu et al., "FDA Perspective on Peptide Formulation and Stability Issues," Nov. 1998, vol. 87, No. 11, J. Pharm. Sciences, pp. 1331-1334.
O'Grady et al. "Guidelines for the prevention of intravascular catheter-related infections. Centers for Disease Control and Prevention." MMWR, Recommendations and Reports, Jul. 2002, vol. 5, No. RR-10, pp. 1-29.
Omnitrope® Highlights of Prescribing Information (dated Jun. 2009).
Padrick et al., "Islet Amyloid Polypeptide: Identification of Long-range Contact and Local Order on the Fibrillogenesis Pathway" J. Mol. Biol., Jun. 2001, vol. 308, No. 4, pp. 783-794.
Parks, "Interactions of the Carboxyl Group of Oleic Acid with Bovine Serum Albumin: a 13C NMR Study", J. Biol. Chem., Issue of Aug. 10, 1983, vol. 258, No. 15, p. 9262-9269.
Payne, Robert W., and Mark Cornell Manning. "Peptide formulation: challenges and strategies." Innov Pharm Technol, 2009, vol. 28, pp. 64-68.
Rapoport, S. I. "Microinfarction: osmotic BBB opening or microcrystals in infusate?" Journal of neurosurgery, Apr. 1991, vol. 74, No. 685.
Robblee et al. "Hypoxemia after intraluminal oxygen line obstruction during cardiopulmonary bypass." the Annals of thoracic surgery, 1989, vol. 48, No. 4, pp. 575-576.
Schellekens H. "Bioequivalence and the immunogenicity of biopharmaceuticals." Jun. 2002, Nature reviews Drug discovery. vol. 1, No. 6, pp. 457-462.
Shanbhag et al., "Interaction of Human Serum Albumin with Fatty Acids Role of Anionic Group Studied by Affinity Partition", Jan. 1979, Eur. J. Biochem. vol. 93, pp. 363-367.
Strauss et al., "A pan European epidemiologic study of insulin injection technique in patients with diabetes" Practical Diabetes Int'l, Apr. 2002, vol. 19, No. 3, pp. 71-76.
Strickley, "Parenteral Formulations of Small Molecules Therapeutics Marketed in the United States (1999)—Part I" Nov.-Dec. 1999, vol. 53, No. 6, PDA J. Pharm. Sci. & Tech. pp. 324-349.
Suzuki et al. "Sequelae of the osmotic blood-brain barrier opening in rats", J. Neurosurg, Sep. 1988, vol. 69 , No. 3, pp. 421-428.
Thorens et al."Glucagon-like peptide-I and the control of insulin secretion in the normal state and in NIDDM." Diabetes, Sep. 1993, vol. 42, No. 9, pp. 1219-1225.

(56) References Cited

OTHER PUBLICATIONS

Tomiwa et al., "Reversible Osmotic Opening of the Blood-Brain Barrier", ACTA PATHOL. JPN, May 1982, vol. 32, No. 3, pp. 427-435.
U.S. Food & Drug Admin., New and Revised Draft Q&As on Biosimilar Development and the BPCI Act (Revision 2), Guidance for Industry, Dec. 2018, pp. 1-17, https://www.fda.gov/regulatory-information/search-fda-guidance-documents/new-and-revised-draft-qas-biosimilar-development-and-bpci-act-revision-2.
U.S. Appl. No. 08/918,810, filed Aug. 26, 1997.
U.S. Appl. No. 11/786,095, filed Jun. 27, 2002.
U.S. Appl. No. 12/785,861, filed Jun. 27, 2002.
U.S. Appl. No. 09/038,432, filed Aug. 26, 1997.
U.S. Appl. No. 09/258,750, filed Aug. 26, 1997.
U.S. Appl. No. 10/185,923, filed Jun. 27, 2002.
U.S. Appl. No. 11/435,977, filed Nov. 18, 2004.
U.S. Appl. No. 60/082,802, filed Apr. 23, 1998.
U.S. Appl. No. 60/084,357, filed May 5, 1998.
U.S. Appl. No. 60/308,297, filed Jul. 27, 2001.
U.S. Appl. No. 60/308,325, filed Jul. 27, 2001.
U.S. Appl. No. 60/524,653, filed Nov. 24, 2003.
U.S. Appl. No. 60/035,904, filed Jan. 24, 1997.
Development and Manufacture of Protein Pharmaceuticals, 2002, Kluwer Academic/Plenum Publishers, pp. 47-127, 129-189.
Dubost et al., "Characterization of a Solid State Reaction Product from a Lyophilized Formulation of a Cyclic Heptapeptide. a Novel Example of an Excipient-Induced Oxidation," Pharmaceutical Research, 1996, vol. 13, No. 12, pp. 1811-1814.
Edwards et al., "Peptides as Drugs," Q J Med, 1999, vol. 92, pp. 1-4.
Expert Declaration of Laird Forrest, Ph. D. in Support of Petition for Inter Parties Review of U.S. Pat. No. 8,114,833, dated Dec. 29, 2019.
FDA Guidance for Industry, Drug Product—Chemistry, Manufacturing, and Controls, 2003, pp. 1-61.
Fox et al., "Ability to handle, and patient preference for, insulin delivery devices in visually impaired patients with type 2 diabetes," Practical Diabetes Int, 2002, vol. 19, No. 4, pp. 104-107.
Fransson et al., "Local Tolerance of Subcutaneous Injections," Journal of Pharm. Pharmacol., 1996, vol. 48, pp. 1012-1015.
Gatlin, "Formulation and Administration Techniques to Minimize Injection Pain and Tissue Damage Associated with Parenteral Products," Injectable Drug Development, 1999, pp. 401-421.
Gerweck et al., "Cellular pH Gradient in Tumor versus Normal Tissue: Potential Exploitation for the Treatment of Cancer," Cancer Research, Mar. 1996, vol. 56, pp. 1194-1198.
Gnanalingham et al., "Accuracy and Reproducibility of Low Dose Insulin Administration Using Pen-Injectors and Syringes," Arch Dis Child, 1998, vol. 79, pp. 59-62.
Griffin et al., "Polyhydric Alcohols," CRC Handbook of Food Additives (Thomas E. Furia, 2nd Edition), 1972, Chapter 10, pp. 431-455.
Handbook of Pharmaceutical Excipients, Fourth Edition, 2003, pp. 257-259, 373-377, 521-523, 574-576, 577-578.
Jacobs, "Factors Influencing Drug Stability in Intravenous Infusions," the Journal of Hospital Pharmacy, Dec. 1969, vol. 27, pp. 341-347.
Madshus, "Regluation of Intracellular pH in Eukaryotic Cells," Biochem. J., 1988, vol. 250, pp. 1-8.
Napaporn et al., "Assessment of the Myotoxicity of Pharmaceutical Buffers Using an in Vitro Muscle Model: Effect of pH, Capacity, Tonicity, and Buffer Type," Pharmaceutical Development and Technology, 2000, vol. 5, No. 1, pp. 123-130.
Noel, "Statistical Quality Control in the Manufacture of Pharmaceuticals," Quality Engineering, 1992, vol. 4, No. 4, pp. 649-657.
Note for Guidance Specifications: Test Procedures and Acceptance Criteria for New Drug Substances and New Drug Products: Chemical Substances (CPMP/ICH/367-96), May 2000, pp. 1-32.
PDA Journal of Pharmaceutical and Science Technology, "Points to Consider for Cleaning Validation," Technical Report No. 29, Aug. 1998, vol. 52, No. 6, pp. 1-23.
Pharmacuetics—The Science of Dosage Form Design (Michael E. Aulton ed., 2nd Edition), 2002, pp. 113-138, 334-359, 544-553.
Prosecution history excerpts for U.S. Pat. No. 8,114,833, Issued Feb. 14, 2012.
Remington's Pharmaceutical Sciences, 18th Edition, 1990, pp. 207-227, 228-246, 257-309, 495-528, 697-724, 725-745, 746-756, 757-773, 1286-1329, 1349-1364, 1435-1458, 1481-1498, 1513-1518, 1519-1544, 1545-1569, 1570-1580, 1596-1614.
Robinson et al., "Subcutaneous versus intravenous administration of heparin in the treatment of deep vein thrombosis; which do patients prefer? a randomized cross-over study," Postgrad Med. J., 1993, vol. 69, pp. 115-116.
Roe et al., "Dose Accuracy Testing of the Humalog/Humulin Insulin Pen Device," Diabetes Technology & Therapeutics, 2001, vol. 3, No. 4, pp. 623-629.
Schade et al., "The Intravenous, Intraperitoneal, and Subcutaneous Routes of Insulin Delivery in Diabetic Man," Diabetes, Dec. 1979, vol. 28, pp. 1069-1072.
Stranz et al., "A Review of pH and Osmolarity," International Journal of Pharmaceutical Compounding, May/Jun. 2002, vol. 6, No. 3, pp. 216-220.
Sturis et al., "GLP-1 derivative liraglutide in rats with b-cell deficiencies: influence of metabolic state on b-cell mass dynamics," British Journal of Pharmacology, 2003, vol. 140, pp. 123-132.
U.S. Pharmacopeia XXII, National Formulary XVII, 1990, pp. 1470-1623.
WIPO Patentscope PCT Bibliography Data for PCT/DK2004/000792 (WO2005049061), filed Nov. 18, 2004.
Zhou et al., "Peptide and protein drugs: I. Therapeutic applications, absorption and parenteral administration," International Journal of Pharmaceutics, 1991, vol. 75, pp. 97-115.
Knudsen et al., "The discovery and development of liraglutide and semaglutide," Frontiers in Endocrinology, Apr. 2019, vol. 10, Article 155, pp. 1-32.
Prickett et al., "Potentiation of Preservatives (Parabens) in Pharmaceutical Formulations by Low Concentrations of Propylene Glycol," Journal of Pharmaceutical Sciences, Apr. 1961, vol. 50, No. 4, pp. 316-320.
Rowe et al., "Propylene Glycol," Handbook of Pharmaceutical Excipients, London/Chicago: Pharmaceutical Press, 2003, Ed. 4, pp. 521-522.
Experimental Report on influence of speed of mixing on fibrillation tendency, dated Dec. 4, 2019, pp. 1-2.
Approved Drug Products With Therapeutic Equivalence Evaluations, 39th ed. 2019, current as of Dec. 31, 2018.
Bates et al., "pH of Aqueous Mixtures of Potassium Dihydrogen Phosphate and Disodium Hydrogen Phosphate at 0° C to 60° C," J. Research Nat'l Bureau Standards, Apr. 1945, vol. 34, pp. 373-394.
Covington, "Definition of PH Scales, Standard Reference Values, Measurement of pH and Related Terminology," Pure & Appl. Chem., 1985, col. 57, No. 3, pp. 531-542.
French et al., "What is a Conservative Substitution?," J. Molecular Evolution, 1983, vol. 19, pp. 171-175.
Kieffer et al., "Degradation of Glucose-Dependent Insulinotropic Polypeptide and Truncated Glucagon-Like Peptide 1 in vitro and in vivo by Dipeptidyl Peptidase IV," Endocrinology, 1995, vol. 136, pp. 3585-3596.
Novo Nordisk—Product Portfolio (Espicom Business Intelligence Ltd. Sep. 28, 2004).
Novo Nordisk FlexPen (2002).
Novo Nordisk Form 6-K (Feb. 20, 2003).
Novo Nordisk NovoLog Mix 70/30 FlexPen prefilled syringe (2002).
Novo Nordisk Press Release, Danish Novo Nordisk Launches Two New Drugs in Three European Countries (ADP Nordic News Mar. 26, 2002).
Novo Nordisk Press Release, New Insulin Analog Formulation with Disposable Prefilled Doser from Novo Nordisk is Now Available in the United States; NovoLog(R) Mix 70/30 FlexPen(R)—Insulin Therapy Made Easy (PR Newswire Assoc., Inc. Sep. 30, 2002).
Novo Nordisk Press Release, Novo Nordisk Launches New Insulin Analogue in US (MDIS Pubs. Oct. 2, 2002).

(56) References Cited

OTHER PUBLICATIONS

Orskov et al., "Biological Effects and Metabolic Rates of Glucagon-like Peptide-1(7-36) Amide and Glucagonlike Peptide-1(7-37) in Healthy Subjects are Indistinguishable," Diabetes, May 1993, vol. 42, pp. 658-661.
Shen et al., "Pharmacokinetics and Biodistribution of PAL-BBI, a Fatty Acid-Polypeptide Conjugate," Proceedings of the Int'l Symposium on Controlled Release of Bioactive Materials, 1996, vol. 23, pp. 887-888.
Wei et al., "Tissue-Specific Expression of the Human Receptor for Glucagon-Like Peptide-I: Brain, Heart and Pancreatic Forms have the Same Deduced Amino Acid Sequences," Febs Letters, 1995, vol. 358, pp. 219-224.
Decision rejecting the opposition dated Feb. 11, 2020 filed in Opposition of EP1687019.
Bummer & Koppenol, "Chemical and Physical Considerations in Protein and Peptide Stability", in Protein Formulation and Delivery, 2000, Chapter 2, pp. 5-69.
"Disodium Hydrogen Phosphate Dihydrate," Chemical Book, available online at http://www.chemicalbook.com/chemicalproductproperty_DE_CB4852564.htm, 3 pages (accessed online Jan. 8, 2018).
Akers et al., "Formulation Development of Protein Dosage Forms," Development and Manufacture of Protein Pharmaceuticals, New York, Kluwer, 2003, pp. 47-127.
Gekko et al., "The stability of protein structure in aqueous propylene glycol: Amino acid solubility and preferential solvation of protein," Biochimica et Biophysica Acta (BBA)—Protein Structure and Molecular Enzymology, 1984, vol. 786, No. 3, pp. 151-160.
Gekko, "Hydration-structure-function relationships of polysaccharides and proteins," Food Hydrocolloids, 1989, vol. 3, No. 4, pp. 289-299.
Lee, "Biopharmaceutical Formulation," Current Opinion in Biotechnology, 2000, vol. 11, No. 1, pp. 81-84.
Sweetana et al., Solubility Principles and Practices for Parenteral Drug Dosage Form Development, PDA J Pharm Sci and Tech, 1996, vol. 50, pp. 330-342.
Nema et al., "Excipients and their use in injectable products," PDA Journal of Pharmaceutical Sciences and Technology, 1997, vol. 51, No. 4, pp. 166-171.
Doenicke et al., "Osmolalities of Propylene Glycol-Containing Drug Formulations for Parenteral Use, Should Proylene Glycol Be Used as a Solvent?," Anesthesia & Analgesia, 1992, vol. 75, No. 3, pp. 431-435.
Powell et al., "Compendium of Excipients for Parenteral Formulations," PDA J Pharm Sci and Tech, 1998, vol. 52, pp. 238-311.
Krakoff et al., "Use of a Parenteral Propylene Glycol-Containing Etomidate Preparation for the Long-Term Management of Ectopic Cushing's Syndrome," the Journal of Clinical Endocrinology & Metabolism, 2001, vol. 86, No. 9, pp. 4104-4108.
Abstract of Ribel et al., "NN2211: a long-acting glucagon-like peptide-1 derivative with anti-diabetic effects in glucose-intolerant pigs," Eur J Pharmacol., Sep. 13, 2002, vol. 451, No. 2, pp. 217-225.
Arakawa T et al., "The Effects of Protein Stabilizers on Aggregation Induced by Multiple-Stresses," Yakugaku Zasshi, 2003, vol. 123, No. 11, pp. 957-961.
Danish Patent Application PA200301719, filed Nov. 20, 2003.
EPO Board of Appeal Decision T 0235/97-3.3.2, Jan. 10, 2002.
Epperson, "Mannitol Crystallization in Plastic Containers," Am J Hosp Pharm., Nov. 1978, vol. 35, No. 11, p. 1337.
Lottspeich/Zotbas, Bioanalytik, 1998, p. 55.
Modern Pharmaceutics, Fourth Edition, 2002, p. 682.
O'Neil M J et al (eds): The Merck Index—an Encyclopedia of Chemicals, Drugs, and Biologicals. Merck & Co., Inc. Whitehouse Station, NJ, 13th edition 2001, pp. 799/1026/1299/1405/1545.
Pharmaceutical Press and American Pharmaceutical Association, "Handbook of Pharmaceutical Excipients", 2003, pp. 521-522.
Pharmaceuticals and Medical Devices Agency Japan: Victoza Subcutaneous Injection 18 mg—Report on the Deliberation Results. Evaluation and Licensing Division, Pharmaceutical and Food Safety Bureau, Ministry of Health, Labour and Welfare—published: 2009.
Remington: The Science and Practice of Pharmacy, 19th edition, 1995, pp. 1402, 1406 and 1462.
Sebeka H K et al., "Comparative effects of stabilizing additives on the rates of heat inactivation of recombinant human interferon a-2b in solution," Antivir Res., Jan. 2000, vol. 50, pp. 117-127.
Voet: Biochemie, 1994, p. 39.
Voigt: Lehrbuch der pharmazeutischen Technologie, 6. Auflage, 1987, pp. 281/282.
Yu D K et al., "Pharmacokinetics of Propylene Glycol in Humans During Multiple Dosing Regimens," J Pharm Sci., Aug. 1985, vol. 74, No. 8, pp. 876-879.
Danish Patent Application No. PA200301689, filed Nov. 13, 2003.
Appendix A document filed with response of Jul. 20, 2017 in EP04797453.0.
Declaration of Malin Persson, dated Jan. 14, 2019.
Victoza User Guide, 2017.
Scott et al., "Warming Kettle for Storing Mannitol Injection," American Journal of Hospital Pharmacy, 1980, vol. 37, pp. 16-22.
Rowe et al., "Mannitol," Handbook of Pharmaceutical Excipients, Sixth Edition, Pharmaceutical Press, 2009, pp. 424-428.
Agerso et al., "The pharmacokinetics, pharmacodynamics, safety and tolerability of NN2211, a new long-acting GLP-1 derivative, in healthy men," Diabetologia, 2002, vol. 45, pp. 195-202.
Wilken et al., "An Immunoassay for the GLP-1 Derivative NN2211," Diabetologia, 2000, vol. 43, Suppl 1, p. 413.
Ludwig, et al., "The 3D structure of rat DPPIV/CD26 as obtained by cryo-TEM and single particle analysis," Biochemical and Biophysical Research Communications, 2003, vol. 304, pp. 73-77.
Ribel et al., "Glucose lowering of the protracted GLP-1 derivative, NN2211, in the Betacell Reduced Minipig," Diabetologia, 2000, vol. 43, Suppl 1, p. 560.
Speth et al., "Propylene Glycol Pharmacokinetics and Effects after Intravenous Infusion in Humans," Therapeutic Drug Monitoring, 1987, vol. 9, No. 3, pp. 255-258.
Younes et al., "Re-evaluation of propane-1,2-diol (E 1520) as a food additive," EFSA Journal, 2018, vol. 16, No. 4:5235, pp. 1-40.
Gaunt et al., "Long-term Toxicity of Propylene Glycol in Rats," Fd Cosmet. Toxicol., 1972, vol. 10, pp. 151-162.
Declaration of Ms. Dorte Kot Engelund dated Dec. 4, 2019.
Excipient Toxicity and Safety, 1st Edition, CRC Press, 2000, pp. 15-16.
A Dictionary of Chemistry (excerpts), 1996 , pp. 80-81.
Akiyama et al., "Comparison of behavior in muscle fiber regeneration after upivacaine hydrochloride- and acid anhydride-induced myonecrosis," Acta Neuropathol, 1992, vol. 83, pp. 584-589.
Alfred Martin, Physical Pharmacy, 4th Edition, 1993, pp. 125-142, 169-189, 212-250.
Asakura et al., "Occurrence of Coring in Insulin Vials and Possibility of Rubber Piece Contaimination by Self-Injection," Yakugaku Zasshi, 2001, vol. 121, No. 6, pp. 459-463.
Banker et al., "Principles of Drug Absorption," Modern Pharmaceutics, 3rd Edition, 1996, pp. 21-73, 75-119, 155-178, 179-211, 213-237, 239-298, 441-487.
Bontempo, Development of Biopharmaceutical Parenteral Dosage Forms, 1997, pp. 91-142.
Borchert et al., "Particulate Matter in Parenteral Products: a Review," Journal of Patenteral Science and Technology, Oct. 1986, vol. 40, No. 5, pp. 212-241.
Bothe et al., "Peptide Oligomerization Memory Effects and Their Impact on the Physical Stability of the GLP-1 Agonist Liraglutide," Mol. Pharmaceutics, 2019, vol. 16, pp. 2153-2161.
Burke et al., "The Adsorption of Proteins to Pharmaceutical Container Surfaces," International Journal of Pharmaceutics, 1992, vol. 86, pp. 89-93.
Chang et al., "NMR studies of the aggregation of glucagon-like peptide-1: formation of a symmetric helical dimer," FEBS Letters, 2002, vol. 515, pp. 165-170.
Tolman R C , The Effect of Droplet Size on Surface Tension , Journal of Chemical Physics. 1949 vol 17, p. 333 . http://scitation.aip.org/content/aip/journal/jcp/17/3/10.1063/1.1747247.
Ashworth MRF, Analytical Methods for Glycerol, Purely Physical Methods, 1979, p. 63 (Academic Press).

(56) References Cited

OTHER PUBLICATIONS

Glycerine, A Key Cosmetic Ingredient, (Edited by Jungermann E et al. ,Alternatives to glycerine, Propylene Glycol, 1991, p. 409.
Alfonso R. Gennaro, Remington : the science and practice of Pharmacy , 19th edition, 1995 (Mack Publishing Company).
Names, Synonyms, and Structures of Organic Compounds, a CRC reference handbook, (Edited by Lide R D. et al., ) vol. 1, Year 1995, pp. 27 and 491.
CRC handbook of chemistry and physics, 81st Edition, Edited by David R. Lide, Version 2000-2001.
Declaration Dorthe Kot Engelund (inventor) dated Jul. 1, 2015.
Inventor declaration—Dorthe Kot Engelund, Ranbaxy Laboratories Limited dated Aug. 20, 2015.
Inventor declaration—Dorthe Kot Engelund, USV Limited dated Aug. 20, 2015.
Ji et al. (2014) "Insulin Pen Injection Technique Survey in Patients with Type 2 Diabetes in Mainland China in 2010." Current Medical Research and Opinion. vol. 30:6. pp. 1087-1093.
Gibson, Mark. (2009) "Choice of Excipients." Pharmaceutical Preformulation and Formulation. 2nd Edition. p. 328.
Chen, Juilette. "The Debate About Needle Reuse" http://www.diabeteshealth.com/blog/the-debate-about-needle-reuse/ Accessed Jan. 9, 2015.
Jiajia Ji, Qingqing Lou (2014), Insulin Pen Injection Technique survey in patients with type 2 diabetes in Mainland China in 2010, Current Medical Research and Opinion. Feb. 2014; 30(6).
Bahar Vardar, Incidence of lipohypertrophy in diabetic patients and a study of influencing factors, Diabetes Research and Clinical Practice 77 (2007) 231-236.
Pharmaceutical Preformulation and Formulation, Second Edition, Mark Gibson, Informa Healthcare USA, Inc., p. 328, 2009.
Clear and colorful Figures 1-7 of the patent ZL200480034152.8, granted Feb. 25, 2015.
The report excerpts including some chromatograms from patent ZL200480034152.8, granted Feb. 25, 2015.
Pharmacopoeia of China 2000 Edition, Chemical Industry Press, vol. 2, pp. 378-381, Apr. 2001.
Pharmacopoeia of China 2000 Edition, Chemical Industry Press, vol. 2, p. 94, Jan. 2000.
Pharmaceutics, Edition 4, People's Health Publishing House, pp. 198-199 and 240, Jul. 2002.
Pharmaceutical Excipients, Edition 1, Luo Mingsheng et al., Sichuan Education Publishing House, Jan. 1995, pp. 18-19, 46-48, 63-68 and 300-302.
Powell MF, Sanders LM, Rogerson A, Si V. Pharmaceutical Research, vol. 8, No. 10, 1991 entitled "Parenteral peptide formulations: chemical and physical properties of native luteinizing hormone-releasing hormone (LHRH) and hydrophobic analogues in aqueous solution" pp. 1258-1263.
Excerpts from the file wrapper of corresponding EP application i.e. EP1687019, dated Oct. 21, 2013.
E-Register of Indian Patent 257402, filed Nov. 18, 2004.
INPADOC patent family 6683 Jun. 11, 2014.
Relevant pages of prosecution history of Counterpart EP Patent Application EP11157594, filed Mar. 10, 2011.
Relevant pages of prosecution history of Counterpart EP Patent Application EP04797453, filed May 19, 2006.
Bibliographic details and the relevant pages of the prosecution history of the counterpart U.S. Appl. No. 13/362,745, filed Jan. 31, 2012.
Affidavit by Dr. Ravindra Agarwal and curriculum vitae dated Feb. 27, 2015.
Affidavit of John F Carpenter and Exhibit, dated Dec. 16, 2014.
Becton, Dickinson and Company Tokoroyo. "Injection Brush Needle." 2015. URL: https://www.bd.com/tw/diabetes/main.aspx?cat=6211&id=6612. Accessed Oct. 30, 2015.
Anand and Anand "Reply Statement and Evidence under section 25(2) of the Patents (Amendment) Act, 2005 and Rule 58 of the Patents (Amendment) Rules 2006" for Novo Nordisk Jan. 6, 2014.
Anand and Anand "Reply Statement and Evidence under section 25(2) of the Patents (Amendment) Act, 2005 and Rule 58 of the Patents (Amendment) Rules 2006" for Novo Nordisk Dec. 30, 2014.
Ken-Chi Izutsu et al. "Effect of Mannitol Crystallinity on the Stabilization of Enzymes During Freeze Drying." Chem. Pharm. Bull. 1994 Vol 42(1) p. 5-8.
Henry Constantino et al. "Effect of Mannitol Crystallization on the Stability and Aersol Performance of a Spray Dried Pharmaceutical Protein, Recombinant Humanized Anti-IgE Monoclonal Antibody." Journal of Pharma. Sci. 1998 vol. 87 (11) pp. 1406-1411.
Raghu K. Cavatur et al. "Crystallization Behaviour of Mannitol in Frozen Aqueous Solutions" Pharmaceutical Research. 2002 vol. 19(6) pp. 894-900.
Somnah Singh et al. "Effects of Polyols on the Conformational Stability and Biological Activity of a Model Protein Lysozyme." AAPS PharmSciTech 2003 vol. 4(3) article 42 pp. 1-9.
Luwei Zhao et al. "Stabilization of Eptifibatide by Cosolvents." International Journal of Pharmaceutics. 2001 vol. 218 pp. 43-56.
Affidavit of Mr. R. Sukumar. Dec. 22, 2015.
R. Sukumar. "Reply to the Declaration of Ms. Dorte Kot Engelund, by way of Affidavit of Mr. R. Sukumar." Dec. 22, 2015.
Affidavit of Omar Sherief Mohammad submitted in USV Opposition dated Jul. 7, 2015.
Federal Register/ vol. 67, No. 236/2002-12-9, pp. 72965-72967.
Case Law of the Boards of Appeal, I.D.9.16., Small improvement in commercially used process. p. 1 URL: https://www.epo.org/law-practice/legal-texts/html/caselaw/2013/e/clr_i_d_9_16.html Last Updated Jan. 10, 2013; Accessed Mar. 31, 2016.
Robyn Rice, Home Care Nursing Practice, Third Edition, Mosby, Inc. 2001, pp. 270-271.
Robyn Rice, Home Care Nursing Practice, Fourth Edition, Mosby, Inc. 2006, p. 273.
Guan Ronglan, Challenging Traditional Insulin Injection Practices, Foreign Medical Sciences (Nursing Foreign Medical Science), 1999, vol. 18 No. 8, pp. 367-368.
Mary MacKinnon RGN, Providing Diabetes Care in General Practice, Third Edition, London : Class Publishing, 1998, p. 111.
American Diabetes Association Complete Guide to Diabetes, American Diabetes Association, 1996, pp. 105-106, 413-414.
Karen Bellenir, Diabetes Sourcebook, Omnigraphics, Inc., 1995, pp. 271-272.
"Horst Ibelgauft's COPE: Cytokines & Cells Online pathfinder Encyclopedia", Insulinotropin, Apr. 2014, pp. 1-2, retrieved from http://www.copewithcytokines.de/cope.cgi?key=insulinotropin.
"Horst Ibelgauft's COPE: Cytokines & Cells Online pathfinder Encyclopedia", GLP-1, Apr. 2014, pp. 1-2, retrieved from http://www.copewithcytokineslde/cope.cgi?key=GLP%2dl.
"DNA Sequence PCR Kits Digest Enzymes DTT Genomic DNA Sequencing PCR Primers RT PCR Protocol", fermantas.com, Apr. 2014, p. 1, retrieved from http://www.fermantas.com/techinfo/appendix/appendixtables1.htm.
Shinotesuto, "Patentabstracts of Japan, of JP10101696", Mar. 2004.
Leaflets of: Trulicity®, Adlyxin®, Sandostatin®, Omontys®, Reference ID: 3107278, Mar. 2012, pp. 1477-1637.
Leaflets of Ozempic and Wegovy and Summary of Wegovy Product Characteristics, Reference ID: 4190425, Dec. 2017, pp. 1649-1822.
Domínguez Avila et al., "The Antidiabetic Mechanisms of Polyphenols Related to Increased Glucagon-Like Peptide-1 (GLP1) and Insulin Signaling", Molecules, May 2017, Vo. 22, No. 6, pp. 1-16.
Makwana et al., "Prefilled syringes: an innovation in parenteral packaging", International Journal of Pharmaceutical Investigation, Oct. 2011, vol. 1, No. 4, pp. 200-206.
Novo Nordisk "Efficacy and Safety of Semaglutide Once-weekly Versus Placebo in Drug-naive Subjects With Type 2 Diabetes (SUSTAIN-1)" NCT clinical trials database, NCT02054897, May 28, 2019, available from https://clinicaltrials.gov/study/NCT02054897?a=28&tab=history.
Novo Nordisk "Efficacy and Safety of Semaglutide Once-weekly Versus Sitagliptin Once-daily as add-on to Metformin and/?or TZD in Subjects With Type 2 Diabetes (SUSTAIN™ 2)" NCT clinical trials database, NCT01930188, May 28, 2019, available from https://clinicaltrials.gov/study/NCT01930188?tab=history&a=25#version-content-panel.

(56) References Cited

OTHER PUBLICATIONS

Novo Nordisk "Efficacy and Safety of Semaglutide Once-weekly Versus Exenatide ER 2.0 mg Once-weekly as add-on to 1-2 Oral Antidiabetic Drugs (OADs) in Subjects With Type 2 Diabetes (SUSTAIN™ 3)" NCT clinical trials database, NCT01885208, May 28, 2019, available from https://clinicaltrials.gov/study/NCT01885208?tab=history&a=32#version-content-panel.
Novo Nordisk "A Trial Comparing the Safety and Efficacy of Semaglutide Once Weekly in Monotherapy or in Combination With One OAD in Japanese Subjects With Type 2 Diabetes (Sustain™)" Nct clinical trials database, NCT02207374, Jun. 21, 2018, available from https://clinicaltrials.gov/study/NCT02207374?tab=history.
Novo Nordisk "Trial to Evaluate Cardiovascular and Other Long-term Outcomes With Semaglutide in Subjects With Type 2 Diabetes (SUSTAIN™ 6)" NCT clinical trials database, NCT01720446, Jun. 20, 2019, available from https://clinicaltrials.gov/study/NCT01720446?tab=history.
Novo Nordisk "Trial Investigating the Effect of Semaglutide on Energy Intake, Appetite Sensations, Postprandial Glucose and Triglyceride Metabolism and Gastric Emptying in Obese Subjects Compared With Placebo" NCT clinical trials database, NCT02079870, Nov. 30, 2017, available from https://www.clinicaltrials.gov/study/NCT02079870? tab=history.
Frokjaer et al., "7.4 Excipient selection, 8.2.1. Buffers", Pharmaceutical Formulation Development of Peptides and Proteins, 2000, pp. 124-125, and 150-151.
"Guideline on Excipients in the Dossier for Application for Marketing Authorisation of a Medicinal Product", EMA, Jun. 19, 2007.
"Note for Guidance on Development Pharmaceutics", EMA, Jan. 28, 1998, 9 pages.
"Note for Guidance on Excipients, Antioxidants and Antimicrobial Preservatives in the Dossier for Application for Marketing Authorisation of a Medicinal Product", EMA, Feb. 20, 2003, 10 pages.
"Note for Guidance on Inclusion of Antioxidants and Antimicrobial Preservatives in Medicinal Products", EMA, Jul. 8, 1997, 5 pages.
"Stability evaluation of pharmaceutical compositions comprising Semaglutide as per patent EP3474820B1", Oct. 31, 2024, 8 pages.
Akers et al., "Drug Delivery: Parenteral Route", Encyclopedia of Pharmaceutical Technology, 2007, vol. 1, Third Edition, pp. 1266-1278.
Akers, "Chapter 26 Parenteral Preparations", Remington: Essentials of Pharmaceutics, 2012, pp. 495-532.
Akers, "Chapter 41 Parenteral Preparations", Remington, The Science and Practice of Pharmacy, 2005, 21st Edition, pp. 802-809.
Bauer, Fromming, Fuhrer," Chapter 9—Parenteralia, einschließlich Blutzubereitungen Sera und Impfstoffe," Lehrbuch der Pharmazeutischen Technologie, 2006, 8th ed., 2006, pp. 238-253.
Bhansali et al., "Historical Overview of Incretin Based Therapies," JAPI, Jun. 2010, vol. 58, pp. 10-14.
Broadhead et al., "Chapter 9—Parenteral Dosage Forms", Pharmaceutical Preformulation and Formulation, 2009, Second Edition, pp. 325-345.
Castillo et al. "Extending residence time and stability of peptides by Protected Graft Copolymer {PGC} excipient: GLP-1 example", Pharm Res., Jan. 2012, vol. 29, No. 1, pp. 306-318.
Company Announcement, "Novo Nordisk files for regulatory approval of once-weekly semaglutide for the treatment of type 2 diabetes in Japan", Novo Nordisk, Feb. 28, 2017, 4 pages.
Company Announcement, "Novo Nordisk reports up to 13.8% weight loss in people with obesity receiving semaglutide in phase 2 trial", Novo Nordisk, Jun. 23, 2017, 2 pages.
European Patent Application No. 17187676.6, filed Aug. 24, 2017, 16 pages.
FDA Highlights of Prescribing Information for TANZEUM, Apr. 2014, 56 pages.
FDA Highlights of Prescribing Information Trulicity® (Dulaglutide), Jan. 2017, 51 pages.
Friedrichs et al., "Injection force of reusable insulin pens: Novopen 4, Lilly Luxura, Berlipen, and ClikSTAR", J Diabetes Sci Technol., Sep. 2011, vol. 5, No. 5, pp. 1185-1190.
Gibson, "Pharmaceutical preformulation and formulation", Informa Healthcare USA, Inc., 2009, 2nd Ed., pp. 329-330.
Hayes et al. "Comparative Effects of the Long-Acting GLP-1 Receptor Ligands, Liraglutide and Exendin-4, on Food Intake and Body Weight Suppression in Rats", Obesity, Mar. 2011, vol. 19, pp. 1342-1349.
Highlights of Prescribing Information for Byetta (exenatide) dated Oct. 2009, 34 pages.
Hribal et al., "Glucagon-like peptide-1 analogs in the treatment of Type 2 diabetes: a review of the Phase II and III trials", Clin. Invest., 2011, vol. 1, No. 2, pp. 327-343.
Jensen et al., "Absorption, metabolism and excretion of the GLP-1 analogue semaglutide in humans and nonclinical species", European Journal of Pharmaceutical Sciences, Mar. 2017, vol. 104, No. 50, pp. 31-41.
Kalra et al., "Glucagon-like peptide-1 receptor agonists in the treatment of type 2 diabetes: Past, present, and future", Indian Journal of Endocrinology and Metabolism, Mar. 2016, vol. 20, pp. 254-267.
Knop et al. "No. Hypoglycemia After Subcutaneous Administration of Glucagon-Like Peptide-1 in Lean Type 2 Diabetic Patients and in Patients With Diabetes Secondary to Chronic Pancreatitis", Diabetes Care, Sep. 2003, vol. 26, pp. 2581-2587.
Label for LYXUMIA (lixisenatide) dated Oct. 2015, 17 pages.
Lorenz et al., "Recent progress and future options in the development of GLP-1 receptor agonists for the treatment of diabesity", Bioorganic & Medicinal Chemistry Letters, May 2013, vol. 23, pp. 4011-4018.
Namkoong et al. "Central administration of GLP-1 and GIP decreases feeding in mice", Biochemical and Biophysical Research Communications, Jun. 2017, vol. 490, pp. 247-252.
Novo Nordisk, "Efficacy and Safety of Semaglutide Versus Dulaglutide as add-on to Metformin in Subjects With Type 2 Diabetes. (SUSTAIN 7)", NCT02648204, Jun. 16, 2017, 28 pages.
Ozempic Assessment Report, EMA, published on Dec. 14, 2017, pp. 1-156.
Wegovy Summary of Product Characteristics, EMA, published in Apr. 2023.
Rowe et al., "Phenol", Handbook of Pharmaceutical Excipients, 2009, Sixth Edition, pp. 485-487.
Zapadka et al. "A pH-Induced Switch in Human Glucagon-like Peptide-1 Aggregation Kinetics." J Am Chem Soc., Dec. 2016, vol. 138, No. 50, pp. 16259-16265.
Zapadka et al., "Factors affecting the physical stability aggregation of peptide therapeutics", Interface Focus, 2017, vol. 7, No. 6, pp. 1-18.
Bokser et al., "Chapter 4 - Stability of Pharmaceutical Products", Remington: Essentials of Pharmaceutics, 2013, 1st Edition, pp. 37-49.
Rowe et al., "Sodium Phosphate, Dibasic and Sodium Phosphate, Monobasic", Handbook of Pharmaceutical Excipients, 2009, Sixth Edition, pp. 659-661.
Nema et al., "Excipients: Parenteral Dosage Forms and Their Role", Encyclopedia of Pharmaceutical Technology, 2007, Third Edition, pp. 1622-1645.
Steele, "Chapter 6 - Preformulation as an Aid to Product Design in Early Drug Development", Pharmaceutical Preformulation and Formulation, 2009, Second Edition, pp. 188-246.
Fda, Full Prescribing Information product Victoza, published 2010.
Snitker et al., "Comparison of the injection-site experience of semaglutide in a single-dose and a multidose pen- injector", Diabetes Obes Metab, May 2022, vol. 24, pp. 1643-1646.

* cited by examiner

GLP-1 COMPOSITIONS AND USES THEREOF

The present invention relates to the field of pharmaceutical compositions comprising the GLP-1 peptide semaglutide.

CROSS-REFERENCE TO RELATED APPLICATIONS

This application is a Track 1 continuation of U.S. application Ser. No. 18/226,405, filed Jul. 26, 2023, which is a continuation of U.S. application Ser. No. 17/115,773, filed Dec. 8, 2020 (U.S. Pat. No. 11,752,198 on Sep. 12, 2023), which is a continuation of U.S. application Ser. No. 16/774,666, filed Jan. 28, 2020 (U.S. Pat. No. 10,888,605 on Jan. 12, 2021), which is a continuation of International Application PCT/EP2018/072835 (WO/2019/038412), filed Aug. 24, 2018, which claims priority to European Patent Application 17187676.6, filed Aug. 24, 2017; the contents of which are incorporated herein by reference.

BACKGROUND

GLP-1 peptides are known to be prone to develop lack of stability in liquid solutions, for example lack of physical stability. Thus, liquid pharmaceutical compositions comprising GLP-1 peptides with even better stability are desired. Such improved stability may be physical stability and/or chemical stability.

SUMMARY

In some embodiments the invention relates to liquid pharmaceutical compositions comprising semaglutide and no more than 0.01% (w/w) phenol. In some embodiments the invention relates to kits comprising the pharmaceutical composition as defined herein. In some embodiments the invention relates to the pharmaceutical composition as defined herein for use in medicine.

DESCRIPTION

The present invention relates to liquid pharmaceutical compositions comprising the GLP-1 peptide semaglutide and no more than 0.01% (w/w) phenol. Surprisingly, the present inventors found that such compositions have improved chemical and/or physical stability. In some embodiments the composition comprises no phenol. n some embodiments the composition comprises 0.01-10 mg/ml semaglutide. In some embodiments the composition has a pH in the range of 6.0-10.0, such as pH 7.0-7.8.

In some embodiments the composition of the invention is a liquid pharmaceutical composition comprising semaglutide and no more than 0.01% (w/w) phenol, wherein said composition
a. is for parenteral administration;
b. is an aqueous solution comprising at least 60% w/w water; or
c. further comprises one or more pharmaceutically acceptable excipients selected from the group consisting of a buffer or an isotonic agent.

In some embodiments the composition of the invention is a liquid pharmaceutical composition comprising semaglutide, no more than 0.01% (w/w) phenol, and optionally one or more pharmaceutically acceptable excipients, wherein the formulation is for parenteral administration, such as subcutaneous administration.

In some embodiments the composition of the invention is a liquid pharmaceutical composition comprising semaglutide, no more than 0.01% (w/w) phenol, at least 60% w/w water, and optionally one or more pharmaceutically acceptable excipients.

In some embodiments the term "stability" as used herein refers to stability of semaglutide in a liquid pharmaceutical composition. In some embodiments stability is chemical stability of the GLP-1 peptide (e.g. determined by HPLC, such as Assay (I) herein), and optionally physical stability of the GLP-1 peptide (e.g. determined by Thioflavine T assay, such as Assay (II) herein).

In some embodiments the term "chemical stability" in relation to semaglutide as used herein refers to the covalent bonds of the semaglutide compound being substantially intact. In some embodiments chemical stability of a GLP-1 peptide is determined by HPLC, such as Assay (I) herein. In some embodiments a composition possess chemical stability if its covalent bonds are intact in at least 80% (w/v) of said GLP-1 peptides after storage for 3 months at 25° C. In some embodiments chemical stability of semaglutide is determined by Assay (IV) herein.

In some embodiments the term "physical stability" in relation to semaglutide as used herein refers to semaglutide forming substantially no aggregates, e.g. in the form of fibril formation. In some embodiments physical stability is determined by Thioflavine T assay, such as Assay (II) herein.

In some embodiments the composition of the present invention is a stable pharmaceutical composition. The term "stable pharmaceutical composition" when used herein refers to a pharmaceutical composition, e.g. a solution or suspension, comprising GLP-1 peptide, and which composition following storage comprises at least 80% (w/v) of said GLP-1 peptide (e.g. after quiescent storage for 3 months at 25° C.). Storage conditions for stability testing may be 2-8° C., such as 5° C., or at least 2.5 years at 5° C. Alternatively, storage conditions for stability testing may be at least 4 weeks, such as 6 weeks or 3 months, optionally at 30° C. The conditions of storage for this stable pharmaceutical composition may be at 5° C. for 1 or 2 years. The conditions of storage for this stable pharmaceutical composition may be at 5° C. for 3 years. Alternatively, the conditions of this storage may be at 25° C. for 24 hours or 1 week. In yet another alternative, the conditions of this storage may be room temperature for two months, such as up to two months.

In some embodiments, chemical stability of the GLP-1 peptide requires at least 80% (w/v), such as at least 90% (w/v) or at least 95% (w/v), of said GLP-1 peptide remaining with its covalent bonds intact at the end of the storage period. In some embodiments chemical stability of the GLP-1 peptide requires at least 95% (w/v), such as at least 97% (w/v) or at least 99% (w/v), of said GLP-1 peptide remaining with its covalent bonds intact at the end of the storage period.

The composition of the invention comprises no more than 0.01% (w/w) phenol. In some embodiments the composition comprises substantially no phenol.

Pharmaceutical Compositions

The terms "pharmaceutical composition" and "composition" are used interchangeably herein and refer to pharmaceutical compositions suitable for administration to a subject in need thereof.

In some embodiments the composition comprises 0.01-100 mg/ml semaglutide. In some embodiments the composition comprises 0.1-50 mg/ml, such as 0.5-25 mg/ml or 1-15 mg/ml, semaglutide. In some embodiments the composition comprises 0.1-10 mg/ml, such as 0.5-5 mg/ml or 1-2 mg/ml, semaglutide. In some embodiments the composition comprises 0.01-10 mg/ml, such as 0.01-5 mg/ml, semaglutide. In some embodiments the composition comprises no more than 9 mg/ml, such as no more than 8 mg/ml or no more than 7 mg/ml, semaglutide. In some embodiments the composition comprises no more than 6 mg/ml, such as no more than 5 mg/ml or no more than 4 mg/ml, semaglutide. In some embodiments the composition comprises no more than 3 mg/ml, such as no more than 2 mg/ml or no more than 1 mg/ml, semaglutide. In some embodiments the composition comprises at least 0.01 mg/ml, such as at least 0.02 mg/ml or at least 0.05 mg/ml, semaglutide. In some embodiments the composition comprises 1.34 mg/ml semaglutide.

In some embodiments the composition of the invention has a pH in the range of 3-10, such as pH 6-10 or 6-9. In some embodiments the composition of the invention has a pH in the range of pH 6.5-8.5, such as pH 7.0-7.8.

In some embodiments the composition of the invention comprises one or more pharmaceutically acceptable excipients.

In some embodiments the composition of the invention comprises an isotonic agent, such as propylene glycol. In some embodiments the isotonic agent is propylene glycol or sodium chloride.

In some embodiments the composition of the invention comprises a buffer, such as phosphate buffer, TRIS, citrate, or no buffer. In some embodiments the phosphate buffer is a sodium phosphate buffer, such as disodium hydrogen phosphate.

In some embodiments the composition of the invention comprises no preservative.

The composition of the invention is in the form of a liquid pharmaceutical composition. In some embodiments the liquid pharmaceutical composition is a solution or a suspension. In some embodiments the composition of the invention is in the form of a solution, such as an aqueous solution. In some embodiments the term "aqueous solution" as used herein refers to a solution comprising at least 60% w/w water. In some embodiments the aqueous solution comprises 60-99% w/w water. In some embodiments the aqueous solution comprises at least 75% w/w water, such as at least 80% w/w water or at least 85% w/w water. In some embodiments the aqueous solution comprises at least 90% w/w water, such as at least 92% w/w water or at least 94% w/w water.

Semaglutide

The GLP-1 peptide semaglutide may be prepared as described in WO2006/097537, Example 4. Semaglutide is also known as $N^{6.26}$-{18-[N-(17-carboxyheptadecanoyl)-L-γ-glutamyl]-10-oxo-3,6, 12, 15-tetraoxa-9, 18-diazaoctadecanoyl}-[8-(2-amino-2-propanoic acid), 34-L-arginine]human glucagon-like peptide 1(7-37), see WHO Drug Information Vol. 24, No. 1, 2010. In some embodiments semaglutide may be present in the composition in its fully or partly ionised form; for example one or more carboxylic acid groups (—COOH) may be deprotonated into the carboxylate group (—COO$^-$) and/or one or more amino groups (—NH$_2$) may be protonated into the —NH$_3{}^+$ group. In some embodiments semaglutide is added to the composition in the form of a salt.

Administration and Kits

The composition of the invention is for parenteral administration. In some embodiments the composition is for subcutaneous administration.

In some embodiments the composition of the invention is for administration once weekly. In some embodiments the composition of the invention is for administration once daily, once every second or once every third day.

In some embodiments the invention relates to a kit comprising the pharmaceutical composition as defined herein and instructions for use. In some embodiments the instructions for use comprise the package insert of a drug.

In some embodiments the invention relates to a kit comprising the pharmaceutical composition as defined herein and an injection device. In some embodiments the injection device is selected from the group consisting of a durable pen and a prefilled pen. Examples of durable pens are NovoPen® 4 or NovoPen® 5 (both from Novo Nordisk A/S, Denmark). An example of a prefilled pen is FlexPen® (Novo Nordisk A/S, Denmark).

Indications

In some embodiments the compositions of the invention are for use in medicine. In some embodiments the composition of the invention may be used for the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1c;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying.

In some embodiments the indication is (i). In some embodiments the indication is (ii). In a still further particular aspect the indication is (iii). In some embodiments the indication is type 2 diabetes and/or obesity.

In some embodiments the method or use comprises prevention, treatment, reduction and/or induction in one or more diseases or conditions defined herein. In some embodiments the indication is (i) and (iii). In some embodiments the indication is (ii) and (iii). In some embodiments the invention comprises administration of an effective amount of a GLP-1 peptide. In some embodiments the invention relates to administration of an effective amount of a GLP-1 peptide.

Generally, all subjects suffering from obesity are also considered to be suffering from overweight. In some embodiments the invention relates to a method for treatment or prevention of obesity. In some embodiments the invention relates to use of the composition for treatment or prevention of obesity. In some embodiments the subject suffering from obesity is human, such as an adult human or a paediatric human (including infants, children, and adolescents). Body mass index (BMI) is a measure of body fat based on height and weight. The formula for calculation is BMI=weight in kilograms/height in meters$^2$. A human subject suffering from obesity may have a BMI of ≥30; this subject may also be referred to as obese. In some embodiments the human subject suffering from obesity may have a BMI of ≥35 or a BMI in the range of ≥30 to <40. In some embodiments the obesity is severe obesity or morbid obesity, wherein the human subject may have a BMI of ≥40.

In some embodiments the invention relates to a method for treatment or prevention of overweight, optionally in the presence of at least one weight-related comorbidity. In some embodiments the invention relates to use of the composition for treatment or prevention of overweight, optionally in the presence of at least one weight-related comorbidity. In some embodiments the subject suffering from overweight is human, such as an adult human or a paediatric human (including infants, children, and adolescents). In some embodiments a human subject suffering from overweight may have a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidemia, high cholesterol, and obstructive sleep apnoea.

In some embodiments the invention relates to a method for reduction of body weight. In some embodiments the invention relates to use of the composition for reduction of body weight. A human to be subjected to reduction of body weight according to the present invention may have a BMI of ≥25, such as a BMI of ≥27 or a BMI of ≥30. In some embodiments the human to be subjected to reduction of body weight according to the present invention may have a BMI of ≥35 or a BMI of ≥40. The term "reduction of body weight" may include treatment or prevention of obesity and/or overweight.

In some embodiments, as used herein, specific values given in relation to numbers or intervals may be understood as the specific value or as about the specific value (e.g. plus or minus 10 percent of the specific value).

EMBODIMENTS OF THE INVENTION

The following are non-limiting embodiments of the invention:
1. A liquid pharmaceutical composition comprising semaglutide and no more than 0.01% (w/w) phenol.
2. A liquid pharmaceutical composition comprising semaglutide and substantially no phenol.
3. The composition according to claim 1 or 2, wherein said composition does not comprise phenol.
4. The composition according to any one of the preceding claims, wherein said composition is an aqueous solution comprising at least 60% w/w water, such as at least 70% w/w water or at least 80% w/w water.
5. The composition according to any one of the preceding claims, wherein the concentration of semaglutide is 0.5-10 mg/ml of said composition.
6. The composition according to any one of the preceding claims, wherein said semaglutide is in the form of a pharmaceutically acceptable salt.
7. The composition according to any one of the preceding claims, wherein said composition comprises one or more pharmaceutically acceptable excipients.
8. The composition according to any one of the preceding claims, wherein said composition comprises one or more agents for adjusting pH, such as HCl, NaOH, or acetate.
9. The composition according to any one of the preceding claims, wherein said composition comprises a buffer and/or an isotonic agent.
10. The composition according to any one of the preceding claims, wherein said buffer is present in a concentration of 0.01-50 mM of said composition.
11. The composition according to any one of the preceding claims, wherein said buffer is a phosphate buffer.
12. The composition according to any one of the preceding claims, wherein said phosphate buffer is selected from the group consisting of sodium dihydrogen phosphate, disodium hydrogen phosphate, and sodium phosphate.
13. The composition according to any one of the preceding claims, wherein said isotonic agent is present in a concentration from 8 mg/ml to 50 mg/ml, such as 14 mg/ml to 30 mg/ml, of said composition.
14. The composition according to any one of the preceding claims, wherein said isotonic is propylene glycol.
15. The composition according to any one of the preceding claims, wherein said composition comprises no preservative.
16. The composition according to any one of the preceding claims, wherein said composition has a pH in the range of 6.0-10.0.
17. The composition according to any one of the preceding claims, wherein said composition is for parenteral administration.
18. The composition according to any one of the preceding claims, wherein said composition is for subcutaneous administration.
19. A kit comprising the pharmaceutical composition as defined in any one of the preceding claims and instructions for use.
20. A kit comprising the pharmaceutical composition as defined in any one of the preceding claims and an injection device for administration of said composition to a subject, wherein said injection device is selected from the group consisting of a durable pen and a prefilled pen.
21. A pharmaceutical composition as defined in any one of the preceding claims for use in medicine.
22. The pharmaceutical composition for use as defined in any one of the preceding claims for use in the treatment of diabetes or obesity.
23. A method for the prevention or treatment of diabetes or obesity, wherein the pharmaceutical composition as defined in any one of the preceding claims is administered to a subject in need thereof.

EXAMPLES

General Methods and Characterisation
Preparation of Semaglutide Compositions:
Unless otherwise noted, compositions of semaglutide were prepared by dissolving buffer (e.g. disodiumhydrogenphosphate dihydrate), isotonic agent (e.g. propylene glycol) and optionally preservative (phenol) in water. Semaglutide was dissolved therein, pH was adjusted to 7.4 using sodium hydroxide and/or hydrochloric acid, and the composition was finally sterilised by filtration through a 0.22 μm sterile filter.

Preparation of Liraglutide Compositions:
Unless otherwise noted, compositions of liraglutide were prepared from Solution 1 and Solution 2: Solution 1 was prepared by dissolving buffer (disodiumhydrogenphosphate dihydrate), isotonic agent (mannitol), and optionally preservative (phenol) in water. Solution 2 was prepared by dissolving liraglutide while stirring slowly. Solution 1 and Solution 2 were mixed, pH was adjusted to 8.15 using sodium hydroxide and/or hydrochloric acid, and the composition was finally sterilised by filtration through a 0.22 μm sterile filter.

Assay (I): Determination of High Molecular Weight Proteins (HMWP) Content of Semaglutide Compositions Determination of HMWP content was performed using size exclusion chromatography (SE-HPLC) using a Waters Insulin HMWP column with a mobile phase of sodium chloride, sodium phosphate, phosphoric acid and isopropanol, isocratic elution and detection at 280 nm. Content of HMWP is given in % as the combined area of chromatographic peaks eluting earlier than the semaglutide monomer peak (i.e. HMWP peaks), relative to the total area of HMWP and semaglutide monomer peaks.

Assay (II): Physical Stability of Semaglutide Compositions Assessed Via ThT

The purpose of this assay is to assess the physical stability of a GLP-1 peptide in aqueous solution.

Low physical stability of a peptide or protein may lead to amyloid fibril formation. Fibrils are structurally well-ordered, filamentous macromolecular structures formed by aggregation of soluble proteins and dominated by beta-sheet structure. Mature fibrils are insoluble and are resistant to degradation. For the sake of drug product quality and patient safety, it is desirable to minimize and control fibrillation events in pharmaceutical compositions of therapeutic peptides and proteins. Protein aggregation, including fibrillation, can be assessed by visual inspection of a sample. Fibrillation can be assessed by the use of Thioflavine T (ThT), a small molecule indicator probe with a high specificity for fibrils. ThT has a distinct fluorescence signature when binding to fibrils compared to ThT in solution [Naiki et al. (1989) Anal. Biochem. 177, 244-249; LeVine (1999) Methods. Enzymol. 309, 274-284].

Formation of a partially folded intermediate of the peptide is suggested as a general initiating mechanism for fibrillation. A small amount of these intermediates nucleates to form a template onto which further intermediates may assembly and the fibrillation proceeds. The lag-time corresponds to the interval in which a critical amount of nuclei is generated and the apparent rate constant is the rate with which the fibril itself is formed. The lag-time described in a ThT assay performed on a plate reader is therefore considered indicative of the fibrillation tendency of a peptide composition in solution.

Before performing the assay, ThT was added to the samples from a stock solution in $H_2O$ to a final concentration of 20 μM in samples. Sample aliquots of 200 μl of the composition comprising the GLP-1 peptide were placed in a 96 well microtiter plate (optical 0.4 mL black Thermo Scientific Nunc) with a glass bead (2.8-3.2 mm, Whitehouse Scientific) placed in each well. Usually, eight replica of each sample were placed on the plate. The plate was sealed with sealing tape (Thermo Scientific Nunc).

Incubation at given temperature, shaking and measurement of the ThT fluorescence emission were performed in a BMG FLUOStar Omega or a BMG FLUOStar Optima. The plate was incubated at 40° C. with double orbital shaking at 300 rpm with an amplitude of 2 mm. Fluorescence measurement was performed using excitation through a 450 nm filter and measurement of emission through a 480 nm filter. The plate was measured every 20 minutes for a desired period of time. Between each measurement, the plate was shaken and heated as described.

The threshold value was determined as the highest ThT fluorescence (in relative fluorescence units (RFU)) measured on the plate at time 1 h 13 min, plus 100 RFU. The threshold value was then used to calculate the lag time using the "time to threshold" method in the BMG FLUOstar software.

Assay (III): Determination of Purity of Liraglutide

Determination of purity was performed using high performance liquid chromatography (HPLC) using a Waters XTerra™ MS C18 column with a gradient elution of two mobile phases, where one mobile phase was an aqueous ammonium phosphate buffer (pH 8)/acetonitrile mixture and the other mobile phase was acetonitrile in water. Detection was performed at 215 nm.

Assay (IV): Determination of Sum of Impurities of Semaglutide

Determination of purity of semaglutide is performed using reversed phase high performance liquid chromatography (RP-HPLC) using a Kinetex C18 column with an isocratic elution followed by a gradient elution of two mobile phases, where one mobile phase was an aqueous phosphate buffer/acetonitrile mixture and the other mobile phase was an aqueous acetonitrile/isopropanol mixture. Detection was performed at 210 nm. Purity of semaglutide is given as sum of impurities in % as the combined area of all chromatographic peaks relative to semaglutide monomer peaks.

Example 1: Semaglutide

Compositions comprising semaglutide were tested in this experiment. The tested compositions contained semaglutide (as specified in Table 1), propylene glycol (14 mg/ml), disodiumhydrogenphosphate dihydrate (1.42 mg/ml), and optionally phenol (5.5 mg/ml) (as specified in Table 1), at pH 7.4 in an aqueous solution. These compositions were prepared as described herein in the section General Methods of Preparation. Chemical stability as expressed by HMWP was determined by Assay (I) described herein at start of the experiment and after storage at 25° C., 30° C. or at 37° C. Physical stability as expressed by Thioflavin T (ThT) assay was determined by Assay (II) described herein.

The results are given in Tables 2 and 3. Surprisingly, these results show that physical and chemical stability of semaglutide were improved in compositions without phenol relative to those with phenol. Results shown in Table 3 are an average of 8 samples tested.

TABLE 1

Compositions tested in Example 1

| Composition no. | Description |
| --- | --- |
| 1 | Semaglutide 1 mg/ml, with phenol |
| 2 | Semaglutide 1 mg/ml, without phenol |
| 3 | Semaglutide 1.34 mg/ml, with phenol |
| 4 | Semaglutide 1.34 mg/ml, without phenol |
| 5 | Semaglutide 0.5 mg/ml, without phenol |
| 6 | Semaglutide 0.5 mg/ml, with phenol |
| 7 | Semaglutide 1.0 mg/ml, without phenol |
| 8 | Semaglutide 1.0 mg/ml, with phenol |
| 9 | Semaglutide 2.0 mg/ml, without phenol |
| 10 | Semaglutide 2.0 mg/ml, with phenol |

TABLE 2

Chemical stability of semaglutide compositions, as expressed by content of high molecular weight proteins (HMWP), following storage at different temperatures. A lower HMWP concentration corresponds to a better chemical stability.

| Composition no. | HMWP (%) | | | |
|---|---|---|---|---|
| | 0 months | 25° C. 6 months | 30° C. 3 months | 37° C. 3 months |
| 1 | 0.1 | 2.0 | 1.9 | 4.1 |
| 2 (no phenol) | 0.1 | 0.3 | 0.3 | 0.5 |
| 3 | 0.1 | 1.9 | 1.8 | 3.9 |
| 4 (no phenol) | 0.1 | 0.3 | 0.4 | 0.6 |

TABLE 3

Physical stability of semaglutide compositions as expressed by Thioflavin T (ThT) assay. A longer lag time corresponds to a better physical stability.

| Composition no. | Lag time (hours) |
|---|---|
| 5 (no phenol) | >117 |
| 6 | 19 |
| 7 (no phenol) | >117 |
| 8 | 35 |
| 9 (no phenol) | >117 |
| 10 | 35 |

Example 2 (Reference): Liraglutide

The results of Example 1 are also surprising in view of the fact that the GLP-1 compound liraglutide—contrary to semaglutide—is less chemically stable in a composition without phenol. These results are shown in Table 5.

The results in Table 5 were obtained as follows: Compositions comprising liraglutide were tested. The tested compositions contained liraglutide (as specified in Table 4), mannitol (36.9 mg/ml), disodium hydrogen phosphate (1.42 mg/ml), and optionally phenol (as specified in Table 4), at pH 7.4 in an aqueous solution. These compositions were prepared as described herein in the section General Methods of Preparation. Chemical stability as expressed by purity was determined by Assay (III) described herein at start of the experiment and after storage at 25° C. or at 37° C.

TABLE 4

Compositions tested in Example 2

| Composition no. | Description |
|---|---|
| 11 | Liraglutide (3 mg/ml), without phenol (pH 7.4) |
| 12 | Liraglutide (3 mg/ml), phenol (0.04 mg/ml) (pH 7.4) |
| 13 | Liraglutide (3 mg/ml), phenol (0.16 mg/ml) (pH 7.4) |
| 14 | Liraglutide (3 mg/ml), phenol (0.8 mg/ml) (pH 7.4) |
| 15 | Liraglutide (3 mg/ml), phenol (2.5 mg/ml) (pH 7.4) |

TABLE 5

Chemical stability, as expressed by purity, of compositions comprising liraglutide following storage at different temperatures. A higher purity corresponds to a better chemical stability.

| Composition no. | Purity (%) | | |
|---|---|---|---|
| | 0 months | 3 months at 25° C. | 3 months at 37° C. |
| 11 (no phenol) | 98 | 88 | 72 |
| 12 | 98 | 93 | 80 |
| 13 | 98 | 94 | 81 |
| 14 | 97 | 95 | 83 |
| 15 | 98 | 95 | 84 |

Example 3: Semaglutide—Additional Experiments

Compositions comprising semaglutide were tested in this experiment. The tested compositions contained semaglutide, isotonic agent (propylene glycol (14 mg/ml) or sodium chloride (6.3 mg/ml)), optionally buffer (disodiumhydrogenphosphate dihydrate (1.42 mg/ml) or trisodiumcitrate dihydrate (2.35 mg/ml)), and optionally phenol (5.5 mg/ml or 0.1 mg/ml), at pH 7.0, 7.4 or 7.8 in an aqueous solution; details of each composition tested is shown in Table 6. The compositions were prepared as described herein in the section General Methods of Preparation. Chemical stability as expressed by HMWP was determined by Assay (I) and as expressed by sum of impurities was determined by Assay (IV) described herein at start of the experiment and after storage at 30° C. Physical stability as expressed by Thioflavin T (ThT) assay was determined by Assay (II) described herein.

The results are given in Table 7 and 8. In line with the results of Example 1, these results show that physical stability and chemical stability of semaglutide were improved in compositions without or with low phenol concentration relative to those with phenol at 5.5 mg/ml. The results show that physical stability and chemical stability of semaglutide were also improved in compositions without phenol comprising either the buffer trisodiumcitrate dihydrate or no buffer or isotonic agent sodium chloride, relative to those with phenol. Chemical and physical stability were improved for compositions with 0.1 mg/ml phenol relative to compositions with 5.5 mg/ml phenol and similar to compositions with no phenol. This was demonstrated for compositions with pH 7.0-7.8 and semaglutide concentration 0.1-10 mg/ml.

TABLE 6

Compositions tested in Example 3

| Comp. No. | Semaglutide (mg/ml) | Phenol (mg/ml) | Buffer | Isotonic agent | pH |
|---|---|---|---|---|---|
| 1 | 0.5 | 0 | Phos* | PG** | 7.0 |
| 2 | 0.5 | 0.1 | Phos | PG | 7.0 |
| 3 | 0.5 | 5.5 | Phos | PG | 7.0 |
| 4 | 0.5 | 0 | Phos | PG | 7.4 |
| 5 | 0.5 | 0.1 | Phos | PG | 7.4 |
| 6 | 0.5 | 5.5 | Phos | PG | 7.4 |

TABLE 6-continued

Compositions tested in Example 3

Content of composition

| Comp. No. | Semaglutide (mg/ml) | Phenol (mg/ml) | Buffer | Isotonic agent | pH |
|---|---|---|---|---|---|
| 7 | 0.5 | 0 | Phos | PG | 7.8 |
| 8 | 0.5 | 0.1 | Phos | PG | 7.8 |
| 9 | 0.5 | 5.5 | Phos | PG | 7.8 |
| 10 | 10 | 0 | Phos | PG | 7.0 |
| 11 | 10 | 0.1 | Phos | PG | 7.0 |
| 12 | 10 | 5.5 | Phos | PG | 7.0 |
| 13 | 10 | 0 | Phos | PG | 7.4 |
| 14 | 10 | 0.1 | Phos | PG | 7.4 |
| 15 | 10 | 5.5 | Phos | PG | 7.4 |
| 16 | 10 | 0 | Phos | PG | 7.8 |
| 17 | 10 | 0.1 | Phos | PG | 7.8 |
| 18 | 10 | 5.5 | Phos | PG | 7.8 |
| 19 | 0.1 | 0 | Phos | PG | 7.4 |
| 20 | 0.1 | 5.5 | Phos | PG | 7.4 |
| 21 | 0.5 | 0 | Phos | Citrate | 7.4 |
| 22 | 0.5 | 5.5 | Phos | Citrate | 7.4 |
| 23 | 0.5 | 0 | Phos | None# | 7.4 |
| 24 | 0.5 | 5.5 | Phos | None | 7.4 |
| 25 | 0.5 | 0 | NaCl## | PG | 7.4 |
| 26 | 0.5 | 5.5 | NaCl | PG | 7.4 |

*Phos: Disodiumhydrogenphosphate dihydrate, 1.42 mg/ml.
**PG: Propylene glycol, 14 mg/ml.
***Citrate: Trisodiumcitrate dihydrate, 2.35 mg/ml.
None: No pharmaceutical excipeints added in the form of a buffer.
NaCl: Sodium chloride, 6.3 mg/ml.

TABLE 8

Physical stability of semaglutide compositions as expressed by Thioflavin T (ThT) assay. A longer lag time corresponds to a better physical stability.

| Composition No. | Semaglutide (mg/ml) | Phenol (mg/ml) | Lag time (hours) |
|---|---|---|---|
| 1 (pH 7.0) | 0.5 | 0 | 42 |
| 2 (pH 7.0) | 0.5 | 0.1 | 63 |
| 3 (pH 7.0) | 0.5 | 5.5 | 5 |
| 4 (pH 7.4) | 0.5 | 0 | >117 |
| 5 (pH 7.4) | 0.5 | 0.1 | >117 |
| 6 (pH 7.4) | 0.5 | 5.5 | 87 |
| 7 (pH 7.8) | 0.5 | 0 | >117 |
| 8 (pH 7.8) | 0.5 | 0.1 | >117 |
| 9 (pH 7.8) | 0.5 | 5.5 | >117 |
| 10 (pH 7.0) | 10 | 0 | 117 |
| 11 (pH 7.0) | 10 | 0.1 | >117 |
| 12 (pH 7.0) | 10 | 5.5 | 25 |
| 13 (pH 7.4) | 10 | 0 | >117 |
| 14 (pH 7.4) | 10 | 0.1 | >117 |
| 15 (pH 7.4) | 10 | 5.5 | >117 |
| 16 (pH 7.8) | 10 | 0 | >117 |
| 17 (pH 7.8) | 10 | 0.1 | >117 |
| 18 (pH 7.8) | 10 | 5.5 | >117 |
| 19 (low DS) | 0.1 | 0 | >117 |
| 20 (low DS) | 0.1 | 5.5 | >117 |
| 21 (citrate) | 0.5 | 0 | >117 |
| 22 (citrate) | 0.5 | 5.5 | >117 |
| 23 (no buffer) | 0.5 | 0 | >117 |
| 24 (no buffer) | 0.5 | 5.5 | 4 |

TABLE 7

Chemical stability of semaglutide compositions, as expressed by content of high molecular weight proteins (HMWP) and sum of impurities, following storage at 30° C. temperature. A lower HMWP concentration and sum of impurities concentration corresponds to a better chemical stability.

| | | | Chemical Stability | | | |
|---|---|---|---|---|---|---|
| | | | HMWP (%) | | Sum of impurities (%) | |
| Composition No. | DS (mg/ml) | Phenol (mg/ml) | 0 months | 30° C. 3 months | 0 months | 30° C. 3 months |
| 1 (pH 7.0) | 0.5 | 0 | 0.1 | 0.3 | 3.1 | 7.0 |
| 2 (pH 7.0) | 0.5 | 0.1 | 0.1 | 0.3 | 3.2 | 7.2 |
| 3 (pH 7.0) | 0.5 | 5.5 | 0.1 | 1.4 | 3.2 | 7.8 |
| 4 (pH 7.4) | 0.5 | 0 | 0.1 | 0.3 | 3.1 | 6.7 |
| 5 (pH 7.4) | 0.5 | 0.1 | 0.1 | 0.3 | 3.2 | 6.6 |
| 6 (pH 7.4) | 0.5 | 5.5 | 0.1 | 2.4 | 3.2 | 8.4 |
| 7 (pH 7.8) | 0.5 | 0 | 0.1 | 0.2 | 3.1 | 6.5 |
| 8 (pH 7.8) | 0.5 | 0.1 | 0.1 | 0.3 | 3.2 | 6.6 |
| 9 (pH 7.8) | 0.5 | 5.5 | 0.1 | 4.8 | 3.1 | 10.6 |
| 10 (pH 7.0) | 10 | 0 | 0.1 | 1.4 | 3.1 | 8.4 |
| 11 (pH 7.0) | 10 | 0.1 | 0.1 | 0.7 | 3.1 | 7.7 |
| 12 (pH 7.0) | 10 | 5.5 | 0.1 | N/A[1] | 3.0 | N/A[1] |
| 13 (pH 7.4) | 10 | 0 | 0.1 | 0.9 | 3.1 | 7.8 |
| 14 (pH 7.4) | 10 | 0.1 | 0.1 | 0.7 | 3.1 | 6.9 |
| 15 (pH 7.4) | 10 | 5.5 | 0.1 | 0.8 | 3.0 | 6.9 |
| 16 (pH 7.8) | 10 | 0 | 0.1 | 0.9 | 3.0 | 6.6 |
| 17 (pH 7.8) | 10 | 0.1 | 0.1 | 0.6 | 3.1 | 6.8 |
| 18 (pH 7.8) | 10 | 5.5 | 0.1 | 1.0 | 3.1 | 6.9 |
| 19 (low DS) | 0.1 | 0 | 0.1 | 0.2 | 3.5 | 7.7 |
| 20 (low DS) | 0.1 | 5.5 | 0.1 | 4.7 | 3.7 | 11.4 |
| 21 (citrate) | 0.5 | 0 | 0.1 | 0.2 | 3.1 | 6.2 |
| 22 (citrate) | 0.5 | 5.5 | 0.1 | 2.2 | 3.2 | 7.7 |
| 23 (no buffer) | 0.5 | 0 | 0.1 | 0.2 | 3.2 | 6.9 |
| 24 (no buffer) | 0.5 | 5.5 | 0.1 | 2.3 | 3.2 | 9.3 |
| 25 (NaCl) | 0.5 | 0 | 0.1 | 0.3 | 3.1 | 6.4 |
| 26 (NaCl) | 0.5 | 5.5 | 0.1 | 3.4 | 3.2 | 8.9 |

DS: Semaglutide.
[1]Not physically stable >1 month at 30° C.

TABLE 8-continued

Physical stability of semaglutide compositions as expressed by Thioflavin T (ThT) assay. A longer lag time corresponds to a better physical stability.

| Composition No. | Semaglutide (mg/ml) | Phenol (mg/ml) | Lag time (hours) |
|---|---|---|---|
| 25 (NaCl) | 0.5 | 0 | >117 |
| 26 (NaCl) | 0.5 | 5.5 | 8 |

Results are an average of 8 samples tested.
DS: Semaglutide.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A liquid pharmaceutical composition comprising:
semaglutide;
wherein said composition
 (a) does not contain phenol; and
 (b) is administered parenterally; and
 (c)(i) is an aqueous solution comprising at least 60% (w/w) water or (ii)
further comprises one or more pharmaceutically acceptable excipients selected from the group consisting of a buffer or an isotonic agent; and
wherein the semaglutide is in the range of 0.01 mg/ml-10.0 mg/ml; and
wherein the pH of the composition is in between 7.0 and 7.8.

2. The liquid pharmaceutical composition according to claim 1, wherein the concentration of semaglutide is selected from 0.5-10 mg/ml or 0.01-5 mg/ml of said composition.

3. The liquid pharmaceutical composition according to claim 1, wherein said composition comprises no added pharmaceutical preservative.

4. The liquid pharmaceutical composition according to claim 1, wherein said parenteral administration is subcutaneous administration.

5. A kit comprising the liquid pharmaceutical composition according to claim 1 and instructions for use.

6. A kit comprising the liquid pharmaceutical composition according to claim 1 and an injection device for administration of said composition to a subject, wherein said injection device is selected from the group consisting of a durable pen and a prefilled pen.

7. A method of treating diabetes comprising administering to a subject in need of such method a therapeutically effective amount of the pharmaceutical composition according to claim 1.

8. A method of treating obesity comprising administering to a subject in need of such method a therapeutically effective amount of the pharmaceutical composition according to claim 1.

9. The liquid pharmaceutical composition according to claim 1, wherein said composition has a pH in the range of 7.0-7.4.

* * * * *

UNITED STATES PATENT AND TRADEMARK OFFICE
CERTIFICATE OF CORRECTION

PATENT NO. : 12,214,017 B2
APPLICATION NO. : 18/427270
DATED : February 4, 2025
INVENTOR(S) : Eva Horn Moeller et al.

It is certified that error appears in the above-identified patent and that said Letters Patent is hereby corrected as shown below:

In the Claims

Column 13, Line 20, replace the entire Claim 1 to read as follows:
1. A liquid pharmaceutical composition comprising:
semaglutide;
wherein said composition
    (a) does not contain phenol; and
    (b) is administered parenterally; and
    (c)(i) is an aqueous solution comprising at least 60% (w/w) water or (ii) further comprises one or more pharmaceutically acceptable excipients selected from the group consisting of a buffer or an isotonic agent; and
wherein the semaglutide is in the range of 0.01 mg/ml – 10.0 mg/ml; and
wherein the pH of the composition is in between 7.0 and 7.8.

Signed and Sealed this
Fifteenth Day of April, 2025

Coke Morgan Stewart
*Acting Director of the United States Patent and Trademark Office*